United States Patent [19]
Beatty et al.

[11] Patent Number: 5,726,334
[45] Date of Patent: Mar. 10, 1998

[54] PROCESS FOR THE PREPARATION OF RUTHENIUM HYDROGENATION CATALYSTS AND PRODUCTS THEREOF

[75] Inventors: Richard Paul Beatty, Newark, Del.; Rocco Angelo Paciello, Bad Durkheim, Germany

[73] Assignee: E. I. du Pont de Nemours and Company, Wilmington, Del.

[21] Appl. No.: 716,473

[22] Filed: Sep. 19, 1996

Related U.S. Application Data

[62] Division of Ser. No. 381,696, Jan. 31, 1995, Pat. No. 5,599,962.

[51] Int. Cl.$^6$ .................. C07F 15/00; C07C 209/00; C07C 249/00
[52] U.S. Cl. .................. 556/21; 502/155; 502/162; 564/278; 564/490; 564/491; 564/492; 564/493; 564/494; 568/840; 556/136
[58] Field of Search .................. 556/21, 136; 502/155, 502/162; 564/278, 490, 491, 492, 493, 494; 568/840

[56] References Cited

U.S. PATENT DOCUMENTS

| | | | |
|---|---|---|---|
| 3,152,184 | 10/1964 | Levering | 260/570.9 |
| 3,454,644 | 7/1969 | Dewhirst | 260/570.9 |
| 3,538,133 | 11/1970 | Knoth | 260/429 |
| 4,254,059 | 3/1981 | Grey et al. | 464/492 |
| 4,268,454 | 5/1981 | Pez et al. | 260/439 R |
| 4,362,671 | 12/1982 | Diamond et al. | 260/465.5 R |
| 4,482,760 | 11/1984 | Kleeman et al. | 568/811 |
| 4,810,825 | 3/1989 | Matsushita et al. | 568/840 |
| 5,151,543 | 9/1992 | Ziemecki | 558/459 |
| 5,554,778 | 9/1996 | Beatty et al. | 556/22 |
| 5,559,262 | 9/1996 | Beatty et al. | 556/20 |

OTHER PUBLICATIONS

Sabo-Etienne, S. et al, *New J. Chem.*, 18, 175–177 (1994).
Christ, M.L. et al, *Inorg. Chem.*, 33, 5316–5319 (1994).
Chaudret, B. et al, *Organometallics*, 4, 1722–1726 (1985).
Knoth, W.H., *J. Amer. Chem. Soc.*, 94(1), 104–109 (1972).
Armit, P.W., *J. Chem. Soc, Dalton Transactions*, 1663–1672 (1975).
Joshi, A.M. et al, *Inor. Chim. Acta.*, 198–200, 283–296 (1992).
Dehmlow, E.V., Universitat Bielefeld, Germany *Kirk–Othmer Ency. of Chem. Tech.*, 7th Ed., 5, 374–383 (1993).
Grushin, V.V., *Acc. Chem. Res.*, 26, 279–286 (1993).
Albers, M.O. et al, Herbert Kaesz, Ed.–in–Chief, Dept. of Chemistry & Biochemistry, UCLA, *Inorg. Synthesis*, 26, 68–77 (1989).
Tolman, C.A., *Chemical Reviews*, 77(3), 313–348 (1977).
Joshi, A.M. et al, *Progress in Catalysis*, E.C. Sanford et al, Editors, Elsevier Science Publishers B.V., 73, 143–146 (1992).
Yoshida, T. et al, *J.C.S. Chem. Comm.*, 870–871 (1979).
Mizzoni, R.H. et al, *J. of Medicinal Chemistry*, 13(5), 878–882 (1970).
Grey, R.A. et al, *J. Am. Chem. Soc.*, 103, 7536–7542 (1981).
Halpern, J., *Pure & Appl. Chem.*, 59(2), 173–180 (1987).
Arliguie T. et al., *Inorg. Chem.*, 27, 598–9, 1988.
Grushin V. V. et al., *Organomet. Chem.*, 382, 185–9, 1990.
Christ M. L. et al., *Organometallics*, 13, 3800–4, 1994.

*Primary Examiner*—Porfirio Nazario-Gonzalez

[57] ABSTRACT

This invention relates to a process for the preparation of ruthenium complexes of the formula $RuH_2L_2(PR_3)_2$, wherein each L is independently $H_2$ or an additional equivalent of $PR_3$, and each R is independently H, a hydrocarbyl group, or an assembly of at least two hydrocarbyl groups connected by ether or amine linkages, comprising contacting a source of ruthenium and $PR_3$ with gaseous hydrogen in the presence of a strong base, a phase-transfer catalyst, water and an organic solvent; and the use of certain classes of ruthenium complexes as catalysts in hydrogenation, and reductive hydrolysis processes.

41 Claims, 3 Drawing Sheets

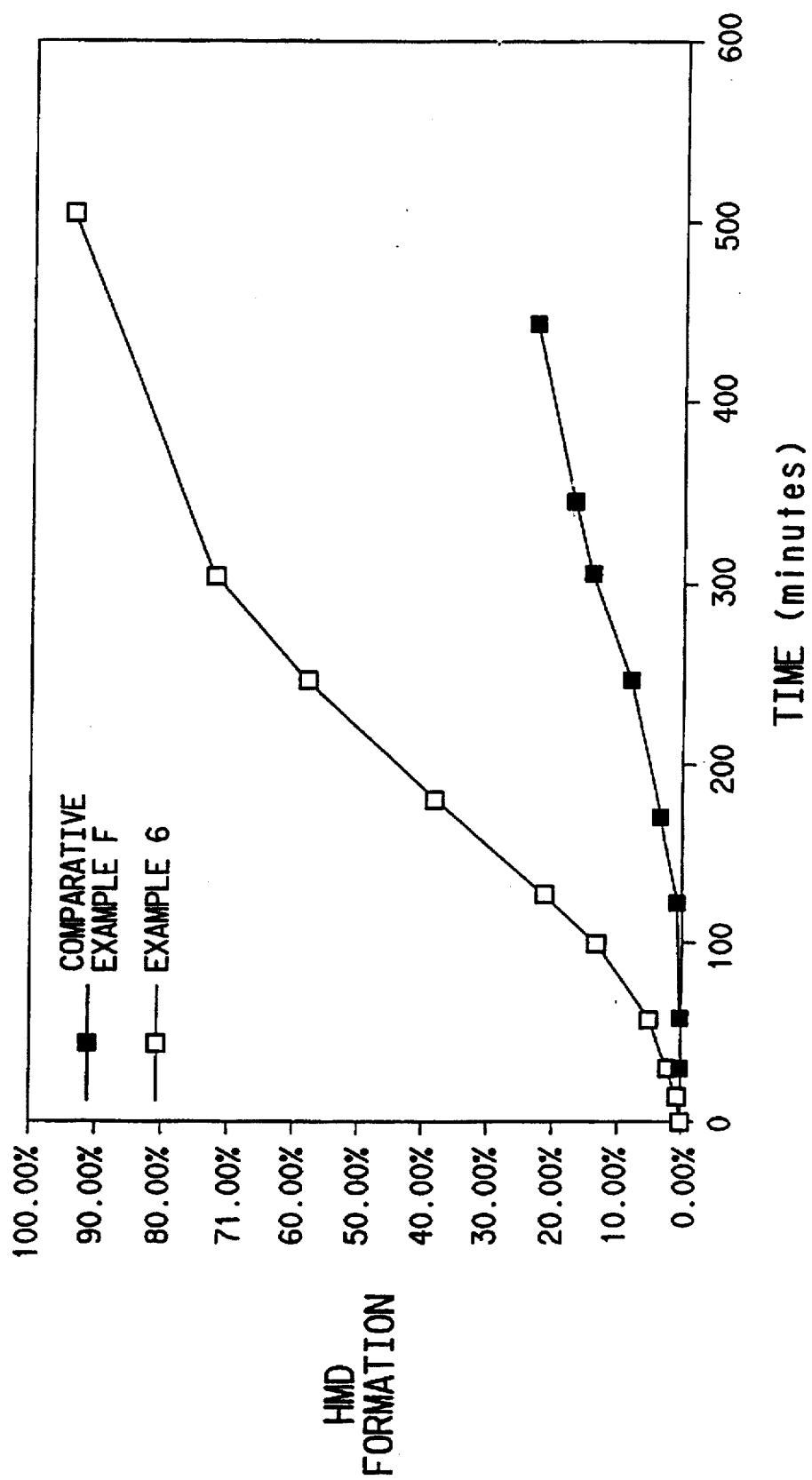

PROCESS FOR THE PREPARATION OF RUTHENIUM HYDROGENATION CATALYSTS AND PRODUCTS THEREOF

This is a division of application Ser. No. 08/381,696, filed Jan. 31, 1995, now U.S. Pat. No. 5,599,962.

FIELD OF THE INVENTION

This invention concerns a process for the preparation of ruthenium complexes, certain novel ruthenium complexes prepared thereby and the use of these ruthenium complexes as catalysts in hydrogenation and hydrolysis reactions.

TECHNICAL BACKGROUND

B. Chaudret and R. Poilblanc, *Organometallics*, 1985, 4, 1722–1726 report the synthesis and characterization of a ruthenium complex, $KuH_6(PCy_3)_2$, later formulated as $RuH_2(H_2)_2(PCy3)_2$ by T. Arligue et al., Inorg. Chem., 1988, Vol. 27, 598–599. The complex was prepared from Ru(COD)(COT). (COD is 1,5-cyclooctadiene, COT is 1,3,5-cyclooctatriene and Cy is cyclohexyl).

A. M. Joshi et al., *Prog in Catal.*, 1992, 73, 143 describe nitrile hydrogenations using di- and tri-nuclear Ru(II) complexes containing chelating diphosphines such as 1,4-bis (diphenylphosphino)butane (dppb). They disclose a preference for $[RuHCl(dppb)]_3$ for nitrile hydrogenations.

SUMMARY OF THE INVENTION

This invention provides a process for the preparation of a ruthenium complex of formula I, $RuH_2L_2(PR_3)_2$, wherein $PR_3$ is a phosphine ligand, each R is a substituent independently selected from H, a hydrocarbyl group, and an assembly of at least two hydrocarbyl groups connected by ether or amine linkages, and each L is a ligand independently selected from $H_2$ or an additional equivalent of the phosphine ligand $PR_3$, wherein each phosphine ligand is present as a separate ligand or cojoined with at least one other phosphine ligand. The complex is prepared by contacting a source of ruthenium preferably (COD)RuCl$_2$ (where COD is 1,5-cyclooctadiene), and $PR_3$ with gaseous hydrogen, in the presence of a strong base, water, a phase transfer catalyst and an organic solvent to form a biphasic medium; agitating the medium; and separating the organic phase comprising the organic solvent and ruthenium complex from the aqueous phase, and optionally isolating the ruthenium complex from the organic solvent.

This invention also provides a novel ruthenium complex of formula II, $RuH_2L^1L_2(PR_3)_2$, wherein $(PR_3)_2$ represents two separate phosphine ligands or a diphosphine ligand, each R is a substituent independently selected from the group consisting of H, a hydrocarbyl group, and an assembly of at least two hydrocarbyl groups connected by ether or amine linkages; $L^1$ is a ligand selected from the group consisting of: $H_2$, $N_2$ and $R^2CN$; $L^2$ is a ligand selected from the group consisting of: $N_2$ and $R^2CN$; and $R^2$ is a hydrocarbyl group. Preferred ruthenium complexes of formula II are those wherein both $L^1$ and $L^2$ are $N_2$.

This invention further provides a process for the hydrogenation of an organic nitrile comprising contacting the nitrite with gaseous hydrogen in the presence of a ruthenium complex catalyst of formula III $RuH_2L^3_2(PR_3)_2$, wherein $PR_3$ is a phosphine ligand, each R is a substituent independently selected from the group consisting of H, a hydrocarbyl group and an assembly of at least two hydrocarbyl groups connected by ether or amine linkages, each phosphine ligand is present as a separate ligand or cojoined with at least one other phosphine ligand, each $L^3$ is a ligand independently selected from the group consisting of $H_2$, $N_2$, $R^2CN$, and an additional equivalent of the phosphine ligand $PR_3$, provided both $L^3$ are not an additional equivalent of $PR_3$, and $R^2$ is an a hydrocarbyl group; and subsequently agitating the nitrite, hydrogen and catalyst to form a primary amine.

The invention also provides a process for the selective hydrogenation of a dinitrile comprising contacting the dinitrile with gaseous hydrogen in the presence of a ruthenium complex catalyst of formula III as described above, and subsequently agitating the dinitrile, hydrogen, and catalyst for an amount of time selected to favor yield of an aminonitrile over yield of a diamine.

This invention further provides a process for the reductive hydrolysis of an organic nitrile comprising contacting the nitrile with gaseous hydrogen and water in the presence of a ruthenium complex catalyst of formula III as described above, and subsequently agitating the nitrile, hydrogen, water and catalyst to form an alcohol.

This invention also provides a process for the selective reductive hydrolysis of a dinitrile comprising contacting the dinitrile with gaseous hydrogen and water in the presence of a ruthenium complex catalyst of formula III as described above, and subsequently agitating the dinitrile, hydrogen, water and catalyst for an amount of time selected to favor yield of a hydroxynitrile over yield of a diol.

BRIEF DESCRIPTION OF THE DRAWINGS

FIG. 3 is a graph comparing hexamethylenediamine (HMD) formation as a function of time for the preferred catalyst of Example 6 and the catalyst of Comparative Example F, run under similar conditions.

DETAILED DESCRIPTION OF THE INVENTION

Figure 1:
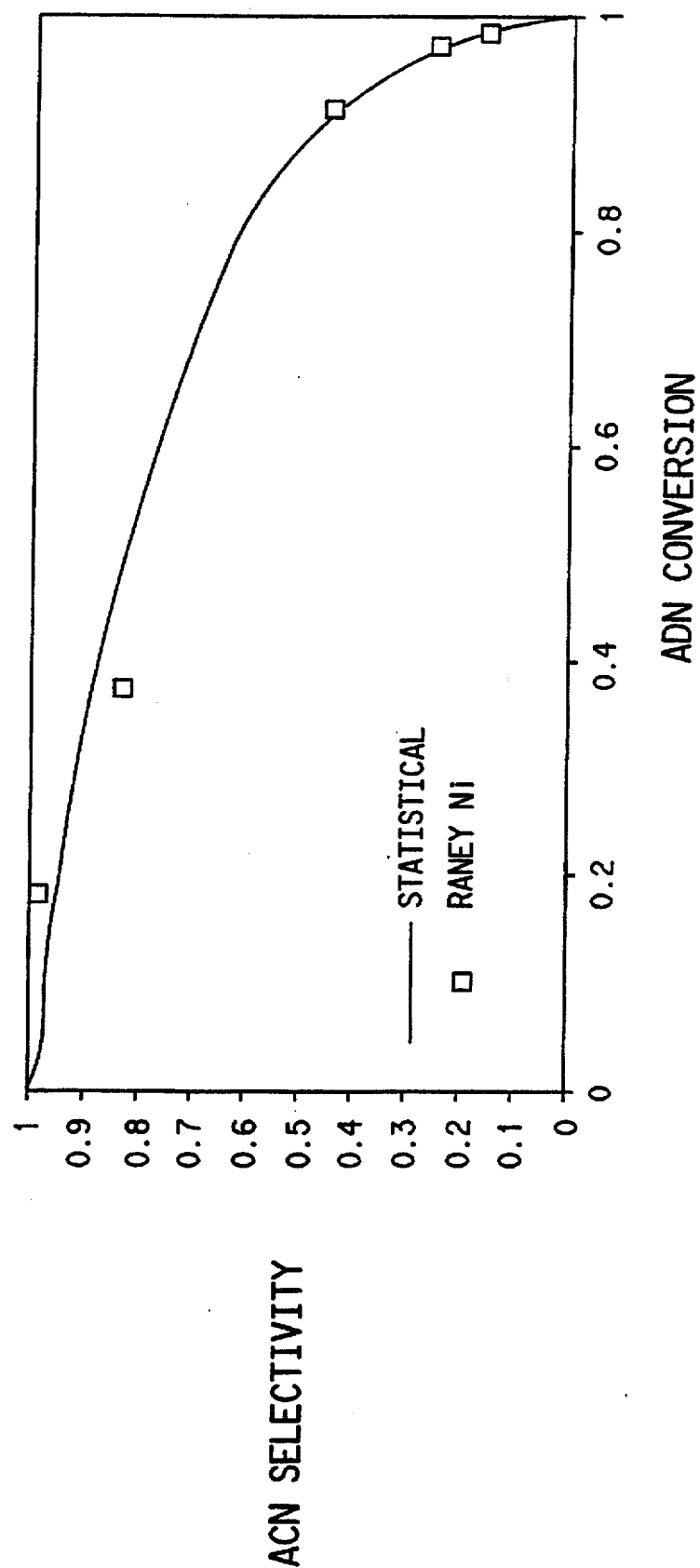
FIG. 1 is a graph showing the aminocapronitrile (ACN) selectivity calculated for an adiponitrile (ADN) hydrogenation, where the two ends of the ADN are assumed to react independently and at the same rate (statistical selectivity) compared to the ACN selectivity actually obtained with a conventional unpromoted Raney Ni catalyst.

This invention provides a process for the preparation of a ruthenium complex of formula I, $RuH_2L_2(PR_3)_2$, comprising contacting a source of ruthenium, such as $(COD)RuCl_2$ and the desired phosphine ligand, $PR_3$, with hydrogen, water, an organic solvent, a strong base, and a phase-transfer catalyst. In formula I, $PR_3$ represents an organophosphine ligand with each R substituent being independently H, a hydrocarbyl group or an assembly of at least two hydrocarbyl groups connected by ether or amine linkages. L represents a ligand independently selected from the group consisting of $H_2$, or an additional equivalent of the phosphine ligand, $PR_3$. Complexes having other L ligands, such as $N_2$ or $R^2CN$, wherein $R^2$ is a hydrocarbyl group can be obtained from those with $L=H_2$ by ligand exchange. Groups of ligands (e.g., two L or two or more $PR_3$ ligands) can represent multidentate ligands. For example, $L_2$ and $(PR3)_2$ can represent 1,4-bis(diphenylphosphino)butane (dppb) in the complex $RuH_2(dppb)_2$.

The process of the present inventions applicable to the preparation of ruthenium complexes having a very broad range of ligands. It provides for preparation of three classes of ruthenium complexes:

| | |
|---|---|
| Class I: | $RuH_2(PR_3)_4$ |
| Class II: | $RuH_2(H_2)(PR_3)_3$ |
| Class III: | $RuH_2(H_2)_2(PR_3)_2$ |

Some complexes of Classes I and II are known but complexes of Class III are rare. Synthesis of known ruthenium complexes were in the past only accessible by complicated and unreliable routes.

The present invention overcomes prior limitations by providing a general route to ruthenium complexes of Classes I, II, and III from common, readily-prepared sources of ruthenium. Sources of ruthenium, for example, bis(alkene) ruthenium(II) compounds, comprise compounds of the formula $R^1{}_2RuX_2$, wherein $R^1$ represents an alkene ligand, and X represents a halide or a pseudohalogen (e.g., the anion of a protonic acid salt, such as nitrate or acetate). The alkene ligands are straight chain, branched, or cyclic arrangements of carbon atoms connected by single, double, or triple carbon-to-carbon bonds, comprising at least one carbon-to-carbon double bond, and substituted accordingly with hydrogen atoms. The alkene ligands can be present either as two separate ligands or as a single polyalkene ligand. Polyalkene ligands such as cycloheptatriene, norbornadiene, and 1,5-Cyclooctadiene (COD) are preferred, with 1,5-cyclooctadiene being the most preferred. Representative examples of bis(alkene)ruthenium(II) compounds comprise (norbornadiene)$RuCl_2$, (cyclohexadiene)$RuCl_2$, and (cycloheptatriene)$RuCl_2$. The preferred bis(alkene) ruthenium(II) compounds are (1,5-cyclooctadiene)$RuX_2$ compounds with (COD)$RuCl_2$ being the most preferred. (COD)$RuCl_2$ can be prepared as described in M. O. Albers, et al., Inorganic Syntheses, 1989, 26, p. 68.

In formula I, $PR_3$ represents an organophosphine ligand, hereafter termed a "phosphine," wherein each R is a substituent independently selected from the group consisting of H, a hydrocarbyl group optionally substituted with fluorine, and an assembly of at least two hydrocarbyl groups connected by ether or amine linkages. By hydrocarbyl group is meant a straight-chain, branched, or cyclic arrangement of carbon atoms connected by single, double, or triple carbon-to-carbon bonds and substituted accordingly with hydrogen atoms. Optionally, the hydrocarbyl group in addition to substitution with hydrogen atoms can be substituted with fluorine. Hydrocarbyl groups can be aromatic and/or aliphatic, for example, phenyl, aryl, alkyl, cycloalkyl, alkenyl, cycloalkyl, alkynyl, and aralkyl. Assemblies of hydrocarbyl groups comprise for example, alkoxy, aryloxy, pyridyl, and aminoalkyl. Suitable hydrocarbyl groups and assemblies of hydrocarbyl groups comprise methyl, ethyl, propyl, isopropyl, butyl, isobutyl, tert-butyl, octylcyclopropyl, cyelobutyl, cyclopentyl, methylcylopentyl, cyclohexyl, methylcyclohexyl, benzyl, phenyl, napthyl, o-tolyl, m-tolyl, p-tolyl, xylyl, vinyl, allyl, butenyl, cyclohexenyl, cyclooctenyl, β-methoxyethyl, 4-methoxybutyl, 2-pyridyl, 4-(N,N-dimethylamino)butyl, and 2-methoxyphenyl.

Suitable phosphine ligands-comprise cyclohexylphosphine, phenylphosphine, diethylphosphine, dicyclohexylphosphine, diphenylphosphine, trimethylphosphine, triethylphosphine, tri-n-propylphosphine, tri-isopropyl-phosphine, tri-n-butylphosphine, tri-isobutylphosphine, tri-t-butylphosphine, triphenylphosphine, tricyclohexylphosphine, tribenzylphosphine, tris(2-pyridyl)-phosphine, tri-p-tolylphosphine, tris(p-trifluoromethylphenyl)phosphine, o-diphenylphosphino-N,N-dimethylaniline, (3-N,N-dimethylammopropyl)di-isopropylphosphine, (4-N,N-dhnethylaminobutyl)di-isopropylphosphine, diphenylmethylphosphine, dimethylphenylphosphine, dicyclohexyl(β-methoxy-ethyl)phosphine, and bis(β-methoxyethyl)phenylphosphine.

Two or more phosphine ligands can be cojoined forming diphosphines, triphosphines, or polyphosphines. Examples of such cojoined ligands comprise 1,2-bis(dimethylphosphino)ethane, 1,2-bis(diethylphosphino)ethane, 1,2-bis-(dicyclohexylphosphino)ethane, bis(dicyclohexylphosphino)methane, 1,2-bis-[(β-methoxyethyl)phosphino]ethane, 1,2-bis(diphenylphosphino)ethane, 1,3-bis(diphenylphosphino)propane, 1,4-bis(diphenylphosphino)butane, 1,2 -bis(diphenylphosphino )benzene, (−)-1,2 -bis((2R,5R)-2,5-dimethyl-phospholano)benzene, (R)-(+)-2,2'-bis(diphenylphosphino)1,1'-binapthyl, bis(2-diphenylphosphinoethyl)phenylphosphine, tris(2-diphenylphosphinoethyl)-phosphine, and 1,1,1-tris(diphenylphosphinomethyl)ethane.

Phosphine ligands can also be attached to various polymer supports. Examples comprise the triphenylphosphine-on-styrene-divinylbenzene copolymers sold by Strem and Aldrich and the triorganophosphine-functionalized polysiloxanes (Deloxan® sold by Degussa AG, Hanau, Germany). Many other similar appropriate supports are known.

The particular class of ruthenium complex produced by the current invention depends, to a large extent, on the steric bulk of the phosphine(s) employed. The concept of cone angle, described by C. A. Tolman in *Chemical Reviews*, 1977, Vol. 77, pp 313–348,is a valuable tool for classifying phosphine ligands and understanding how their steric bulk determines which class of complex is obtained. Small ligands, with cone angles of about 130° or less, such as the tri-n-alkylphosphines, including, for example, tributylphosphine, favor formation of complexes of Class I. Intermediate size ligands, with cone angles of 140°–150°, favor formation of complexes of class II. Large ligands, with cone angles of 160°–180°, favor formation of complexes of Class III. Since each R substituent on $PR_3$ can be varied independently, the steric bulk of $PR_3$ can be varied continuously over a wide range. Since steric size can be continuously varied, the boundaries between the classes of the ruthenium complexed are not sharply delineated. As a consequence, in the process of the present invention for cases where complexes of Class II can be produced; mixtures are often obtained comprising, in addition, some complexes of Class I or Class III. In such cases, the exact composition of the mixture obtained can be controlled, to some extent, by adjusting the molar ratio of phosphine ligand to ruthenium compound used in the preparation. For example, where mixtures of Class I and Class II complexes are obtained, formation of Class I complexes can be favored by using a large excess of phosphine ligand in the preparation while formation of Class II complexes can be favored by using only three $PR_3$ per ruthenium, i.e., little or no excess of phosphine ligand. Similar considerations apply to controlling mixtures of Class II and III complexes. Complexes of Class III can be favored by using only two $PR_3$ per ruthenium while those of Class II can be favored by using three or more $PR_3$ per ruthenium. complexes of Class II and III are preferred for hydrogenation reactions. Complexes of class III are especially preferred, and especially those with large phosphines which substantially prevent formation of complexes of Class II even in the presence of excess phosphine. Complexes of Class III where $PR_3$ is $PCy_3$ are most preferred.

The process of the present invention is applicable to the preparation of ruthenium complexes having a broad range of ligands. Each class of ruthenium complex, i.e., $RuH_2(PR_3)_4$, $RuH_2(H_2)(PR_3)_3$, or $RuH_2(H_2)(PR_3)_2$ has a distinctive NMR pattern, based on symmetry of the complex. For example, with octahedral geometry around Ru, cis-$RuH_2(PR_3)_4$ contains two different types of phosphine ligands: two equivalent phosphines each of which is trans to a H ligand and two equivalent phosphines trans to each other. This leads to a phosphorus NMR spectrum described as an $A_2X_2$ pattern which is understood by one skilled in the art as resulting in a pair of triplets of equal intensity. A complex, but distinctive, multiplet is observed for the hydride signal in the proton NMR and integration should be correct for four phosphine ligands and two hydride H. Representative examples of ruthenium complexes of Class I are $RuH_2(P-nBu_3)_4$, $RuH_2(P-m-tol_3)_4$, $RuH_2(P-p-tol_3)_4$, $RuH_2[P(C_6H_4-p-CF_3)_3]_4$, $RuH_2(dppb)_2$, and $RuH_2(R-Me-Duphos)_2$.

$RuH_2(H_2)(PR_3)_3$ typically show only single lines in both the proton and phosphorus NMR due to rapid ligand and $H_2$-hydride exchange, but integration of the proton NMR should be correct for four hydrides and 3 phosphine ligands. One valuable diagnostic for identifying $RuH_2(H_2)(PR_3)_3$ species is their tendency to rapidly exchange $H_2$ for $N_2$ under a dinitrogen atmosphere forming $RuH_2(N_2)(PR_3)_3$, which has a more distinctive NMR signature. The phosphorus NMR shows a $A_2X$ pattern, i.e., a triplet of intensity one and a doublet of intensity two. The proton NMR spectrum comprises a distinctive pair of complex multiplets of equal intensities indicating two non-equivalent hydrides, such as would be expected for an octahedral geometry with one hydride is trans to a phosphine ligand and the other trans to a $N_2$ ligand. $RuH_2(H_2)(PR_3)_3$ can often be recognized by comparing proton and phosphorus NMR spectra of a solution prepared under $H_2$ to a solution prepared under $N_2$. Representative examples of ruthenium complexes of Class II are $RuH_2(H_2)(PPh_3)_3$, $RuH_2(H_2)[P(p-tol)_3]_3$, $RuH_2(H_2)[P(C_6H_4-p-CF_3)_3]_3$, $RuH_2(H_2)(P-iBu_3)_3$, $RuH_2(H_2)(P-m-tol_3)_3$, $RuH_2(H_2)(P-iPr_3)_3$, $RuH_2(H_2)(P-benzyl_3)_3$, $RuH_2(H_2)(PPh_{2,P}-tol)_3$, and $RuH_2(H_2)(Cy_2PCH_2CH_2OCH_3)_3$.

Finally, $RuH_2(H_2)_2(PR_3)_2$ show a single line phosphorus NMR spectrum. Under high resolution conditions, the hyride signal in the proton NMR spectrum appears as a triplet due to coupling to two equivalent phosphine ligands, and the relative intensities of the hydride and ligand protons integrate correctly for a ratio of six hydrides and 2 phosphine ligands. $RuH_2(H_2)_2(PR_3)_2$ complexes can also be distinguished by their tendency to exchange $H_2$ for $N_2$ to form $RuH_2(N_2)2(PR_3)_2$. These novel dinitrogen complexes of the present invention display a single line in their proton-decoupled phosphorus NMR which becomes a triplet with proton coupling, confirming the presence of two hydrides. The hydride signal in the proton NMR appears as a triplet with coupling to two equivalent phosphorus nuclei. Formation of $RuH_2(H_2)_2(PR_2)_2$ can be proven by its reaction with nitrogen to give $RuH_2(N_2)2(PR_3)_2$ which can be followed by comparing proton and phosphorus NMR spectra of a solution prepared under $H_2$ to a solution prepared under $N_2$. Representative examples of ruthenium complexes of Class III are $RuH_2(H_2)_2(P-iPr_3)_2$, and $RuH_2(H_2)_2(PCy_3)_2$.

The process of the present invention is conducted in biphasic media, comprising a strongly basic aqueous phase and an organic solvent phase which comprises the ruthenium starting material. The organic solvent should be immiscible with the aqueous phase and unreactive toward the starting materials and products. Aprotic solvents, commonly defined as those with autoprotolysis equilibria constants less than about $10^{-20}$, are preferred. Hydrocarbon solvents, such as benzene or toluene, are especially preferred.

A base is added to the aqueous Phase to maintain pH >11, preferably >12. The base can be either organic or inorganic, but it must be soluble in the aqueous phase and not have an appreciable solubility in the organic phase. Other than maintaining a high enough pH for the reaction to occur, the only other requirement for the base is that it not participate in undesired reactions with other reactants or solvents. The preferred bases are the Group I or II hydroxides, for example, LiOH, NaOH, KOH, and $Ca(OH)_2$, with NaOH being most preferred. Stronger bases can be used if desired, but because of their leveling effect in water, these bases will function equivalently to hydroxide. For example, sodium hydride is a much stronger base than sodium hydroxide, but in water it is instantly converted to hydrogen and sodium hydroxide.

The success of the present process depends on reaction of the aqueous base hydroxides (e.g., NaOH) have essentially no solubility in organic media and the ruthenium reactants have essentially no solubility in the aqueous caustic phase, therefore the desired reaction does not occur at an acceptable rate in the absence of a phase transfer catalyst (PTC).

One broad class of phase transfer catalyts useful in the present process can be represented as $Q^+Y^-$, where $Q^+$ represents a cation and $Y^-$ an anion. This type of phase transfer catalyst comprises, for example, quaternary ammonium halides (e.g., benzyl triethyl ammonium chloride, tetrabutyl ammonium bromide) and tetraalkyl phosphonium halides (e.g., tetrabutyl phosphonium chloride). Another broad class of phase transfer catalyst comprises linear and cyclic polyethers or polyether amines (e.g., polyalkylene glycols, Crown ethers, and Cryptands such as Kryptofix 222®, a product of E. M. Science, Gibbstown, N.J.). Any of these phase transfer catalysts are suitable in the present process provided that they do not participate in undesired reactions with solvents or other reactants. A preferred phase transfer catalyst is benzyltriethylammoninm chloride since it is relatively inexpensive, widely used and readily available.

Phase transfer catalysts are believed to function by forming ion pairs which have higher solubility in the organic phase of the two-phase reaction than the ion pairs present in the absence of the phase transfer catalyst. For example, NaOH has very low Solubility in organic media. In the presence of a quarternary salt phase transfer catalyst $(Q^+Y^-)$, ion pairs such as $Q^+OH^-$ can form which have higher solubility in the organic phase, greatly enhancing reaction rate. In essence, the phase transfer catalyst acts to transport the reactive anion to the organic phase, where it can participate in the desired reaction. Crown ethers, Cryptands, polyalkalene glycols, and other neutral phase transfer catalysts are believed to function by complexing or encapsulating the aqueous cation, again forming an ion pair with enhanced organic solubility (e.g., K. Crown ether $^+OH^-$), which can be transported into the organic phase for reaction. In the organic phase, the ruthenium compound is thought to fist react with phosphine ligands and hydrogen to generate reactive intermediates containing dihydrogen or hydride ligands as well as X ligands. Hydroxide anion, transported into the organic phase by the phase transfer catalyst as $Q^+OH^-$, is thought to react with these intermediate ruthenium species by abstracting $H^+X^-$, forming water, a new ruthenium species, and a new ion pair $Q^+X^-$. The exact mechanism by which this occurs is unknown, and is not important to successful application of this method. $Q^+X^-$ the X migrates back to the aqueous phase, releasing $X^-$ and picking up another $OH^-$ to repeat the cycle.

The phase transfer catalyst is used in catalytic amounts. The preferred amount of phase transfer catalyst is about 1% to about 10% on a molar basis compared the amount of ruthenium compound used. Smaller amounts of phase transfer catalyst can be used, but require longer reaction times. Larger amounts can also be used, but result in increased cost.

The source of hydrogen comprises hydrogen gas or a mixture of hydrogen gas with inert gases such as $N_2$, He, Ne, or Ar. Pure gaseous hydrogen is preferred. Mixtures comprising carbon monoxide, such as "synthesis gas" are not acceptable, since CO reacts with the desired ruthenium complex to produce a carbonyl complex.

Because of the biphasic medium, effective agitation is required in order to provide sufficient contact of the gaseous hydrogen with the organic phase for the hydrogenation reaction to occur and to provide sufficient contact of the aqueous and organic phases for the phase transfer catalyst to function.

The temperature range employed is from about $-30°$ C. to about $200°$ C. The preferred range is about $20°$ C. to about $100°$ C.

The partial pressure of hydrogen should be between about 100 kPa and about 15000 kPa. The preferred pressure is from about 700 kPa to about 7000 kPa. Higher pressures can be used, but are not required and generally do not justify the expense of the more exotic equipment required.

The organic phase comprising the ruthenium complex can be separated from the aqueous phase by decantation. The aqueous phase can be extracted with additional portions of solvent to increase recovery of the ruthenium complex from the aqueous phase. The resulting organic phase comprising the ruthenium complex can then be optionally washed with water to improve removal of residual base. The resulting organic phase comprising the ruthenium complex is generally used as a catalyst without further treatment. If desired, the ruthenium complex can be isolated by one of a variety of methods, such as evaporation of solvent, crystallization by cooling, or precipitation by addition of a second organic solvent which is a poor solvent for the ruthenium complex. The exact isolation procedure depends on the amount and nature of the organic solvent used in the preparation. It is desirable to maintain a hydrogen atmosphere as much as possible during manipulation and isolation of the ruthenium complex to avoid loss of hydrogen from the ruthenium complex.

The present invention provides a novel ruthenium complex of formula II, $RuH_2L^1L^2(PR_3)_2$ wherein each R is a substituent independently selected from the group consisting of H; a hydrocarbyl group, as defined above for formula I; and an assembly of at least two hydrocarbyl groups connected by ether or amine linkages, as defined above for formula I; $L^1$ is a ligand selected from the group consisting of $H_2$, $N_2$ and $R^2CN$; $L^2$ is a ligand selected from the group consisting of $N_2$ and $R^2CN$; and $R^2$ is hydrocarbyl group or a hydrocarbyl group substituted with non-interfering substituents comprising hydroxyl, ester, amide, amine, ether, alkoxy, aryloxy, aldehyde, imine and nitro. Certain ruthenium complexes of formula I, specifically those wherein both L are not $PR_3$, e.g., $RuH_2(H_2)(PR_3)_3$ and $RuH_2(H_2)(PR_3)_2$, can be used to prepare complexes of formula II.

Dihydrogen ligands present in certain ruthenium complexes of formula I can be displaced by dinitrogen ligands. In complexes where both L are $H_2$, either one or both L can be displaced by dinitrogen, forming either $RuH_2(H_2)(N_2)(PR_3)_2$ or $RuH_2(N_2)_2(PR_3)_2$, hereafter referred to as "dinitrogen complexes." For example, sparging a solution of $RuH_2(H_2)_2(PCy_3)_2$ with nitrogen gas, thereby removing hydrogen from solution, results in rapid and quantitative conversion into $RuH_2(N_2)_2(PCy_3)_2$. This stable bis (dinitrogen) complex, which represents a completely new class of ruthenium complexes, was isolated and unambiguously characterized by x-ray crystallography. It contains two cis-hydride ligands, two cis-dinitrogen ligands, and two trans-tricyclohexylphosphine ligands arranged octahedrally around ruthenium.

Dinitrogen complexes are often more stable than dihydrogen complexes, for example, when catalyst is placed under a protective nitrogen atmosphere during storage, during preparation of feeds for a reaction, or during product separation or catalyst recycle.

Solvents which are useful in preparation of the dinitrogen complexes of the present invention should not themselves be capable of displacing L ligands from $RuH_2L_2(PR_3)_2$ tol form complexes incorporating the solvent. Suitable solvents for preparation of dinitrogen complexes are hydrocarbons, comprising $C_6$–$C_{12}$ non-fused benzenoid hydrocarbons and $C_1$–$C_{18}$ alkyl derivatives thereof and $C_1$–$C_{30}$ linear or branched saturated aliphatic or alicyclic hydrocarbons. Mixtures of hydrocarbons can also be used such as "petroleum ether," typically characterized by boiling range. By the term non-fused benzenoid hydrocarbons is meant that of more than one benzene ring is present in the hydrocarbon, the rings are isolated, not fused together. Thus, the term encompasses biphenyl but not naphthalene. Especially preferred solvents comprise toluene, pentane, hexane, and petroleum ether with a boiling range of about $35°$ to about $60°$ C.

Agitation is required to ensure adequate gas-liquid mass transfer, including both dissolution of dinitrogen gas into the reaction solution and loss of dihydrogen from the solution, and can be provided by any convenient method, such as stirring or gas sparging.

The temperature employed for this reaction is normally between about $-80°$ C. and about $100°$ C. The preferred temperature is from about $15°$ C. to about $30°$ C. Higher temperatures increase reaction rate but adversely affect stability of the ruthenium complexes.

Pressure is not an important variable; normal atmospheric pressure is preferred, though higher or lower pressure can be employed of desired.

The reaction time required is determined mainly by the efficiency of contacting and removal of dihydrogen from the reaction mixture. With temperatures below about $30°$ C., reaction time is not critical; reaction times longer than the minimum essential time can be employed since the dinitrogen complexes are stable at those temperatures. With reaction temperatures above about $30°$–$40°$ C., reaction time should be kept at an empirically determined minimum avoid unnecessary decomposition of the dinitrogen complexes. Progress of the reaction can be followed spectroscopically by IR or NMR with phosphorus NMR berg particularly useful. Once the minimum essential reaction time is determined in this way, it will remain constant as long as reaction conditions are not changed.

Dihyrogen or dinitrogen ligands complexes $RuH_2(H_2)_2(PR_3)_2$, $RuH_2(H_2)(N_2)(PR_3)_2$, $RuH_2(N_2)_2(PR_3)_2$, $RuH_2(H_2)(PR_3)_3$ and $RuH_2(N_2)(PR_3)_3$ of formula I or formula II can be displaced by other electron pair donor ligands to yield other complexes of formula II or certain complexes of formula III:

$RuH_2L^3{}_2(PR_3)_2$  III wherein:

PR$_3$ is a phosphine ligand wherein R is defined as above for formula I and II, each L$^3$ is an electron pair donor ligand independently selected from the group consisting of: H$_2$, N$_2$, R$^2$CN and an additional equivalent of the phosphine ligand PR$_3$, provided both L$^3$ are not PR$_3$, as defined above for formula II; and wherein each phosphine ligand is present as a separate ligand or cojoined with at least one other phosphine ligand.

Examples of such electron pair donors particularly relevant to the current invention comprise dihydrogen, dinitrogen, and nitriles which are some of the organic reactants of hydrogenation reactions of the present invention. Certain intermediates, products and solvents of hydrogenation reactions of the present invention which can also give as electron pair donors comprise alcohols, mines, imines, ethers aldehydes ketones, esters, mides, alkenes and alkynes, For the complexes RuH$_2$(H$_2$)$_2$. (PRi)$_2$ and RuH$_2$(N$_2$)$_2$(PR$_3$)$_2$, either one or both of the dihydrogen or dinitrogen ligands can be displaced by added electron pair donors to form the RuH$_2$L$^3{}_2$(PR$_3$)$_2$ complex of formula III or other ruthenium complexes with above mentioned electron pair donor ligands. In some cases, mixtures of ruthenium complexes can be obtained incorporating two or more different electron pair donor ligands. It is not necessary to purify such mixtures; they can be used directly in hydrogenation reactions. For example, the RuH$_2$L32(PR$_3$)$_2$ complex formed when the added electron pair donor ligands are nitriles, hereafter referred to as "nitrile complexes," need not be purified before use in hydrogenations. NMR and IR spectra of nitrile complexes typically indicate the presence of hydride, phosphine, dinitrogen, and nitrite ligands. Representative nitrile complexes prepared rising acetonitrile, propionitrile, valeronitrile, and adiponitrile are described in the examples. Nitrile complexes can be preformed or can form in situ on mixing catalyst with nitriles in a hydrogenation reaction.

Solvents which are usable in the preparation of the RuH$_2$L32(PR$_3$)$_2$complex of formula III comprise those described above for preparation of dinitrogen complexes as well as the added ligand, L$^3$, itself provided it is a liquid at the reaction temperature and is capable of dissolving the reactants sufficiently for reaction to take place.

Temperature, pressure, and agitation requirements are as described above for preparation of dinitrogen complexes. The preferred temperature and pressure are ambient, i.e., about 15° C. to about 25° C. and 1 atmosphere. It is not necessary for the reactants to be completely dissolved for reaction to occur. As long as there is some solubility and sufficient. agitation, the reaction will take place. Normally ligand exchange is rapid, complete within minutes after mixing. The product complexes can be isolated by removal of solvent and filtration, or may be used without isolation.

If the reaction mixture is. allowed to remain in contact beyond the time required for ligand exchange, and especially when temperatures above ambient are employed, secondary reactions can occur. For example, in the presence of hydrogen, nitrile complexes can be partially hydrogenated to imine complexes. The necessary hydrogen can be added intentionally, or can be that hydrogen released by ligand exchange of a dihydrogen complex. Alternatively, when amines are used in ligand exchange to prepare amine complexes, the amine complex can be dehydrogenated to an imine complex. As shown in Example 34 such imine complexes are themselves useful catalysts. These secondary hydrogenation and dehydrogenation processes can result in mixtures of various nitrile, imine, and amine complexes which can be used without purification in hydrogenation reactions.

The RuH$_2$L$^3{}_2$(PR$_3$)$_2$ complexes of formula III described above may be more stable under certain conditions than the dihydrogen complexes from which they can be derived. This increased stability facilitates catalyst storage and recycle.

The ruthenium complexes RuH$_2$L$^3{}_2$(PR$_3$)$_2$ of formula III have utility as catalysts. They are useful in catalytic hydrogenation reactions, for example, in the reduction of olefins, in the reduction of nitro compounds to amines and, especially, in the reduction of nitriles, which are generally difficult to hydrogenate catalytically, to amines. The most important commercial use of these catalysts is thought to be in the reduction of adiponitrile to either 6-aminohexanenitrile or to hexamethylene diamine or to mixtures of the two.

The present invention provides a process for the hydrogenation of an organic nitrile comprising contacting the nitrile with gaseous hydrogen in the presence of a ruthenium complex of formula III, as a catalyst. The nitrile, hydrogen, and catalyst are subsequently agitated to form a primary amine.

Suitable nitrile substrates which are applicable in the hydrogenation process of the present invention comprise those having at least one CN group which is capable of being hydrogenated to the corresponding primary amine. Typically, the nitrile substrate is a monomeric material with one or two CN groups. However, the nitrile substrate :can also be oligo- or polymeric, with either regularly occurring or Occasional CN functional groups, comprising, for example, fluoronitriles such as F(CF$_2$CF$_2$)$_n$CH$_2$CH$_2$CN wherein n ranges from 2 to about 6. Complete reduction of a dinitrile to a diamine is a variant of the present hydrogenation process of nitriles.

Suitable nitrile substrates comprise the classes of linear or branched saturated aliphatic C$_2$-C$_{18}$ mono- and C$_3$-C$_{19}$ dinitriles and phenyl derivatives thereof. C$_4$-C$_{13}$ saturated all cyclic mono- and C$_5$-C$_{14}$ dinitriles, C$_3$-C$_{18}$ linear or branched olefinically unsaturated aliphatic nitriles, C$_6$-C$_{13}$ olefinically unsaturated alicyclic nitriles, C$_7$-C$_{14}$ aromatic mono- and dinitriles, C$_6$-C$_8$ heterocyclic nitrogen and oxygen mononitriles, C$_3$-C$_4$ cyanoalkanoic amides, C$_2$-C$_2$ saturated aliphatic cyanohydrins or hydroxynitriles, or mixtures of the above-described nitriles, wherein said nitriles can also contain non-interfering substituents.

Examples of some substituents which generally do not interfere with the desired hydrogenation reaction comprise hydroxl, amine, ether, alkyl, alkoky, and aryloxy. For example, cyanohydrins and hydroxynitriles are both acceptable nitriles. Unsaturated, hydrogenatable substituents such as ester, amide, aldehyde, imine, nitro, alkene, and alkyne are permissable in that they do not interfere with hydrogenation of the nitrile group, but they may themselves be hydrogenated partly or completety in the course of the nitrile hydrogenation. For example, 2-pentenenitrile can be hydrogenated completely to aminopentane. Carboxylic acids are generally not acceptable substituents since they react with the catalyst, deactivating it. Representative examples of specific nitriles applicable in the invention process comprise: acetonitrile (C$_2$) propionitrile (C$_3$), butronitrile (C$_4$), valeronitrile (C$_5$), capronitrile (C$_6$), 2,2-dimethylpropanenitrile, enanthonitrile (C$_7$), caprylonitrile (C$_8$), pelargononitrile (C$_9$), caprinitrile (C$_{10}$), hendecanenitrile (C$_{11}$), lauronitrile (C$_{12}$), tridecanenitriles (C$_{13}$), myristonitrile (C$_{14}$), pentadecane-nitrile (C$_{15}$), palmitonitrile (C$_{16}$), margaronitrile (C$_{17}$), stearonitrile (C$_{18}$), phenyl-glutaronitrile, 2-methylglutaronotrile, adipontrile, acrylonitrile, methacrylonitrile, 2-methyleneglutaronitrile, 1,4-dicyano-2-butene, 1,4-dicyano-1-butene, dodecanedinitrile, 3-butenenitrile, 4-pentenenitrile, 3-pentenenitrile, 2-pentenenitrile, 2-hexenenitrile, 2-hepterienitrile, glycolonitrile (formaldehyde cyanohydrin), hydracrylonitrile (ethylene cyanohydrin), eqi-cyanohydrin (gamma cyanopropylene oxide), lactonitrile, pyruvonitrile, cyclohexanecarbonitrile, cyclododecanecarbonitrile, benzonitrile, o-tolylnitrile, m-tolylnitrile, p-tolylnitrile, anthranilonitrile, m-aminobenzonitrile, p-aminobenzonitrile, 1-napthonitrile, 2-napthonitrile, phthalonitrile, isophthalonitrile, terephthalonitrile, mandelonitrile, 2-pyridinenitrile, 3-pyridinenitrile, 4-pyridinenitrile, or 2-furylacetonitrile.

Preferred nitriles in the process are adipontrile, 2-methylglutaronitrile, and dodecanedinitrile.

The process Can be conducted in the neat state, i.e., no solvent, provided that the nitrile and product amine are liquids at the reaction temperature employed and that the catalyst is sufficiently soluble therein. However, use of a solvent is preferred to facilitate contacting of the reactants and removal of heat. The solubility of the respective materials in the solvent (or mixture of solvents) should be significantly large enough to initiate and maintain the hydrogenation process.

Solvents which are usable in these hydrogenation processes must be inert towed hydrogenation under the reaction conditions and possess adequate solvating ability for the substrate nitrile and catalyst.

Although the solvent employed is normally and preferably anhydrous, this is not a strict requirement. While the amount of water present is normally, and preferably, less than about 0.01 mole of water per mole of nitrile, larger amounts of water, up to about 0.1 to about 1 mole of water per mole of nitrile, generally do not produce significant amounts of alcohol by-products. In the case of a hydrophobic nitrile and hydrophobic solvent, large amounts of water, even a second liquid phase, can be present and do not interfere with normal hydrogenation. Suitable solvents comprise $C_6$–$C_{12}$ non-fused benzenoid hydrocarbons and $C_1$–$C_{18}$ alkyl derivatives thereof, $C_5$–$C_{30}$ linear or branched saturated aliphatic or alicyclic hydrocarbons, $C_2$–$C_{12}$ aliphatic ethers, $C_4$–$C_{12}$ saturated aliphatic cyclic mono or diethers, or $C_7$–$C_{14}$ aromatic ethers, or mixtures thereof. By the term "non-fused benzenoid hydrocarbons" is meant that if more than one benzene ring is present in the hydrocarbon, the rings are isolated and not fused together. Thus, the term encompasses biphenyl, but not naphthalene.

Suitable solvents further comprise amines, especially those amines produced by hydrogenation of the above nitriles which are liquid at reaction temperature. Representative examples of specific useful solvents comprise ammonia, methylamine, ethylamine, n-propylamine, isopropylamine, n-butylamine, amylamine, azacycloheptane, 2-methyl-pentamethylenediamine and hexa-methylenediamine, xylene, hexamethylbenzene, biphenyl, n-octadecylbenzene, benzene, toluene, pentane, cyclopentane, cyclohexane, methylcyclohexane, hexane, isooctane, decane, cyclodecane, tetrahydrofuran, p-dioxane, 2,5-dimethyl-tetrahydrofuran, methyl tetrahydrofurfuryl ether, dimethyl ether, 1,2-dimethoxyethane, diglyme, diethyl ether, diisopropyl ether, anisole, diphenylether, and mixtures thereof.

Preferred solvents comprise ammonia, THF, t-butyl methyl ether, toluene, n-amylamine, n-butylamine, 2-methyl-pentamethylenediamine, and hexamethylene-diamine. Most preferred, when the amine product of the hydrogenation is a liquid at reaction temperature, is to use that same amine product as the reaction solvent. For example, butylamine can be used as the solvent when hydrogenating butyronitrile or hexamethylenediamine can be used as the solvent when hydrogenating adiponitrile.

The amount of catalyst used can vary from about 10 mole percent, based on nitrile to be hydrogenated, to about 0.01 mole percent. The preferred amount of catalyst is between about 1% and about 0.1% of the amount of nitrile to be hydrogenated on a molar basis. Larger or smaller amounts of catalyst can be used at the expense of catalyst cost or reaction time respectively. Preferred catalysts for the present hydrogenation process comprise those wherein neither L 3 is $PR_3$. Most preferred are $RuH_2(H_2)_2$, $(PCy_3)_2$, $RuH_2(H_2)_2$ $(PCy_3)_2$, $RuH_2(H_2)_2(P-iPr_3)_2$ and $RUH_2(N_2)_2(P-ipr_3)_2$.

Excess phosphine can be present if desired. Although excess phosphine is not required, the presence of excess phosphine ensures that there is always adequate phosphine to stabilize the ruthenium catalyst, even if adventitious oxygen oxdizes a small amount of phosphine to the corresponding phosphine oxide or other side reactions degrade portions of the phosphine ligand. Phosphine oxide formed in this manner can also be present and does not interfere with hydrogenation reactions. The molar ratio of excess, phosphine to ruthenium compound can vary from zero to about 60 or even more. The preferred molar ratio is between zero and about 30, with a molar ratio of about 2 to about 25 being while higher temperatures reduce catalyst life and reduce the yield of the desired most preferred.

The hydrogenation can be conducted at any convenient temperature, from about 0° C. to about 200° C. Lower temperatures require prolonged reaction times while higher temperatures reduce catalyst life and reduce the yield of the desired primary amine products. The preferred temperature is in the range of about 60° to about 120° C. with about 80° to about 100° C. being most preferred.

The source of hydrogen can be hydrogen gas or mixtures of hydrogen gas with other gases which do not interfere with the desired hydrogenation. Non-interfering gases comprise, for example, inert gases, such as helium, argon, and nitrogen. Oxygen and carbon monoxide should be avoided since they can react with the catalysts.

The pressure employed can be from about 100 kPa (1 atmosphere) to about 15000 kPa or even higher. Elevated pressures are preferred since the solubility of hydrogen is increased which leads to higher reaction rates. However, pressures above about 7000 kPa to about 10000 kPa are generally avoided due to the high cost of equipment capable of operating at such pressures.

The preferred pressure for production of primary amines in high yield is in the range from about 3550 kPa to about 10000 kPa. Pressures between about 5000 kPa and about 7000 kPa are most preferred.

Ruthenium complexes of formula $IIIRUH_2L^3{}_2(PR_3)_2$, are also useful as catalysts for hydrogenation of organic nitro groups to primary amine groups. For example, nitrobenzene can be hydrogenated to aniline. Use of the homogeneous catalysts of the present invention in place of traditional heterogeneous catalysts for nitro group hydrogenation can facilitate heat removal from these highly exothermic hydrogenation reactions and help maintain a uniform reaction temperature, thereby improving yield of the desired primary amine. The process for the hydrogenation of a nitro compound to a primary amine comprises the steps of contacting the nitro compound having at least one $NO_2$ group with gaseous hydrogen in the presence of a ruthenium catalyst of formula III, as a catalyst. The nitro group, hydrogen and catalyst are subsequently agitated to form a primary amine.

Nitro compounds which are applicable to the present invention are those having at least one $NO_2$ group which is capable of being hydrogenated to the corresponding primary amine. Multiple nitro groups can be present. Such nitro compounds can be represented by the formula R'$NO_2$, where R' is $C_1$–$C_{18}$ arrangement of carbon atoms in a linear, branched, or cyclic structure with hydrogen atoms or other non-interfering substituents incorporated as appropriate. Examples of some substituents which generally do not interfere with the desired hydrogenation comprise alkyl, aryl, hydroxyl, amine, ether, alkoxy, and aryloxy. Unsaturated hydrogenatable substituents such as cyano, ketone, aldehyde, ester, amide, alkene and alkyne are permissable in that they do not interfere with hydrogenation of the nitro group, but they may themselves be hydrogenated partly or completely in the course of the nitro group hydrogenation.

The amount of catalyst, excess phosphine, temperature, pressure, solvents, agitation requirements, and sources of hydrogen are as described above for hydrogenation of nitriles to amines. Preferred catalysts for the hydrogenation of organic nitro groups comprise those wherein neither $L^3$ is $PR_3$. Most preferred are $RuH_2(H_2)_2(PCy_3)_2$, $RuH_2(N_2)_2(PCy_3)_2$, $RuH_2(H_2)_2(P\text{-}iPr_3)_2$ and $RuH_2(N_2)_2(P\text{-}iPr_3)_2$.

The hydrogenation of nitriles and nitro compounds is a two-phase reaction. Therefore, it is essential to provide adequate gas-liquid contact to enable the gaseous hydrogen to dissolve in the liquid reaction phase. Adequate gas-liquid contact can be facilitated by any of the various agitation methods familiar to those skilled in the art. Typical methods comprise sparging gas below the liquid surface in a tank reactor, stirring the liquid in a tank reactor to draw gas into the liquid and create bubbles, use of packing in a tower reactor to obtain high liquid surface area, or use of a bubble column reactor, wherein bubbles of gas are introduced into the reactor and rise through the liquid phase.

Complexes of formula III are also useful as catalysts in a selective reduction process wherein a dinitrile is partially hydrogenareal to yield an aminonitrile. For example, the major intermediate in adiponitrile hydrogenation, 6-aminocapronitrile, can be prepared in high yield if the hydrogenation is stopped at an intermediate stage. This amino nitrile can then be directly hydrolyzed and polymerizod to Nylon 6. The process for the selective hydrogenation a dinitrile comprises the steps of contacting the dinitrile with gaseous hydrogen in the presence of a catalyst of formula III and subsequently agitating the dinitrile, hydrogen, and catalyst to form the aminonitrile.

· Linear or branched saturated aliphatic $C_3$ to $C_{19}$ dinitriles and phenyl derivatives thereof, $C_5$ to $C_{14}$ saturated alicyclic dinitriles, $C_7$ to C14 aromatic dinitriles. Aliphatic dinitriles comprising about 6 to about 12 carbon atoms are preferred. The dinitrile used in this hydrogenation process can be any aliphatic dinitrile comprising about 3 to about 14 carbon atoms, but preferably comprising about 6 to about 12 carbon atoms. Preferably, the carbon atoms are arranged in a linear or branched chain. Especially preferred examples of dinitriles and their product comprised adiponitrile hydrogenated to 6-aminocapronitrile, 2-methylglutaronitrile hydrogenated to a mixture of two isomeric aminonitriles (5-amino-2-methyl valeronitrile and 5-amino-4-methyl valeronitrile), and dodecanedinitrile hydrogenated to 12-aminododecanenitrile.

The amount of catalyst, excess phosphine, solvents, temperature, pressure, agitation requirements and sources of hydrogen are the same as discussed above for the hydrogenation of nitriles and nitro compounds to primary amines. Preferred catalysts for the selective reduction process of the present invention comprise those wherein neither $L^3$ is $PR_3$. Most preferred are $RuH_2(H_2)_2(PCy_3)_2$, $RuH_2(N_2)_2(PCy_3)_2$, $RuH_2(H_2)_2(P\text{-}iPr_3)_2$ and $RuH_2(N_2)_2(P\text{-}iPr_3)_2$.

The desired product of the selective reduction, an aminonitrile, is an intermediate in that variant of the present hydrogenation process which eventually results in the formation of a diamine. The aminonitrile concentration in the reacting mixture passes through a maximum as the reaction progresses. One objective of this embodiment of the present invention is to maximize the concentration of the aminonitrile in the reacting mixture at the highest possible conversion of the starting dinitrile. The yield of the aminonitrile and the position of the maximum. With respect to dinitrile conversion depend on operating conditions such as temperature, hydrogen pressure, amount and kind of catalyst, dilution of starting dinitrile, as well as, the type of solvent. These variables in turn influence the optimum contact time for the reaction. Conventional nitrile hydrogenation catalysts such as Raney Ni frequently give aminocapronitrile (ACN) selectivities approximating those expected statistically, assuming the two ends of the dinitrile are hydrogenated independently and at comparable rates. FIG. 1 shows the calculated statistical ACN selectivity along with the selectivity actually obtained using fin unpromoted Raney Ni catalyst (Raney Ni 2800, available commercially from W. R. Grace and co., Baltimore, Md.). In contrast, the catalysts of the process of the present invention give aminonitrile selectivities higher than those expected statistically.

The optimum contact time of the present invention needed to favor formation of an amino nitrile need be determined only, once for any given set of reaction conditions. Once the optimum has been determined, it will remain constant as long as reaction conditions, such as catalyst, reactant concentrations, temperature, and pressure are held constant.

The ruthenium complexes of formula III are also useful as catalysts in a process of the present invention for reductive hydrolysis of an organic nitrile to an as defined above, and subsequently agitating the nitrile, water, hydrogen, and alcohol. The process comprises the steps of contacting the nitrile with gaseous hydrogen and water in the presence of a catalyst of formula III, $RuH_2L^3{}_2(PR_3)_2$, catalyst to form the alcohol. Significantly, dinitriles can be cleanly converted to diols using this process of the present invention. Reductive hydrolyses using the catalysts of formula III in the process of the present invention have been found to be exceptionally clean and specific.

Suitable nitrile substrates which are applicable in the reductive hydrolysis process of the present invention comprise those which comprise at least one CN group capable of being reduced to the corresponding primary alcohol. Typically, the nitrile substrate is a monomeric material with one or two CN groups. However, the substrate can also be oligo- or polymeric, with either regularly occurring or occasional CN functional groups, comprising, for example, fluoronitriles such as, $F(CF_2CF_2)_nCH_2CH_2CN$, wherein n ranges from 2 to about 6. Complete reductive hydrolysis of a dinitrile to a diol is one variant of the present reductive hydrolysis process.

Suitable nitrile substrates comprise the classes of line or branched saturated aliphatic $C_2$–$C_{18}$ mono-and $C_3$–$C_{19}$ dinitriles and phenyl derivatives thereof, $C_4$–$C_{13}$ saturated alicyclic mono- and $C_5$–$C_{14}$ dinitriles, $C_3$–$C_{18}$ linear or branched olefinically unsaturated aliphatic nitriles, $C_6$–$C_{13}$ olefinically unsaturated alicyclic nitrile, $C_7$–$C_{14}$ aromatic mono- and dinitriles, $C_6$–$C_8$ heterocyclic nitrogen and oxygen mononitriles, $C_3$–$C_4$ cyanoalkanoic amides, $C_2$–$C_{12}$ saturated aliphatic cyanohydrins or hydroxynitriles, or mixtures of the above-described nitriles, wherein said nitriles can also contain non-interfering substituents.

Examples of some substituents which generally do not interfere with the desired reduction reaction comprise hydroxyl, amine, ether, alkyl, alkoxy, and aryloxy. For example, cyanohydrins and hydroxynitriles are both acceptable nitriles. Unsaturated, hydrogenatable substituents such as aldehyde, ester, amide, imine, nitro, alkene, and alkyne are permissable in that they do not interfere with reductive hydrolysis of the nitrile group, but they may themselves be hydrogenated or hydrolyzed partly or completely in the course of the nitrile reductive hydrolysis. For example, 2-pentenenitrile can be reductively hydrolyzed completely to 1-pentanol. Carboxylic acids are generally not acceptable substituents since they react with the catalyst, deactivating it.

Representative examples of specific nitriles applicable in the invention process are: acetonitrile ($C_2$), propionitrile ($C_3$), butyronitrile ($C_4$), valeronitrile ($C_5$), capronitrile ($C_6$), 2,2-dimethylpropanenitrile, enanthonitrile ($C_7$), caprylonitrile ($C_8$), pelargononitrile ($C_9$), caprinitrile ($C_{10}$), hendecanenitrile ($C_{11}$), lautronitrile ($C_{12}$), tridecanenitrile ($C_{13}$), myristonitrile ($C_{14}$), pentadecanenitrile ($C_{15}$), palmitonitrile ($C_{16}$), margaronitrile ($C_{17}$), stearonitrile ($C_{18}$), phenylacetonitrile (benzyl nitrile), napthylacetonitrile, malononitrile, succinonitrile, glutaronitrile, 2-methylglutaronitrile, adiponitrile, acrylonitrile, methacrylonitrile, 2-methyleneglutaronitrile, 1,4-dicyano-2-butene, 1,4-dicyano-1-butene, dodecanedinitrile, 3-butenanitrile, 4-pentenenitrile, 3-pentenenitrile, 2-pentenenitrile, 2-hexenenitrile, 2-heptenenitrile, glycolonitrile (formaldehyde cyanohydrin), hydracrylonitrile (ethylene cyanohydrin), eqicyanohydrin (gamma-cyanopropylene oxide, lactonitrile, pyruvonitrile cyclohexanecarbonitrile; cyclododecanecarbonitrile, benzonitrile, o-tolylnitrile, m-tolylnitrile, p-tolylnitrile, anthranilonitrile, m-aminobenzonitrile, p-aminobenzonitrile, 1-napthonitrile, 2-napthonitrile, phthalonitrile, isophthalonitrile, terephthalonitrile, mandelonitrile, 2-pyridinenitrile, 3-pyridinenitrile, 4-pyridinenitrile, or 2-furylacetonitrile.

Preferred nitriles in the process are adiponitrile, 2-methylglutaronitrile, and dodecanedinitrile. Also preferred is 3-cyano methyl isobutyrate which cyclizes on reductive hydrolysis producing 2-methyl-butyrolactone, a useful intermediate for 3-methyl-tetrahydrofuran.

Water is a required reactant in the reductive hydrolysis. At least one mole of water is required per mole of nitrile, but larger amounts are typically used, and quantifies of 2000 moles water per mole nitrile or even more can be used. The preferred amount of water is about 30 to about 300 moles water/mole nitrile. Larger amounts of water enhance selectivity to alcohols but make product isolation more difficult. Smaller amounts of water reduce the selectivity to alcohols, increasing the amount of amines produced.

In general, the same classes of solvents as described above for nitrile hydrogenation are suitable. However, it is essential that adequate water be available to the reacting nitrile to achieve the desired reductive hydrolysis, producing alcohol, rather than simple hydrogenation which would produce amine. There are three possible modes of operation: (a) neat, i.e., without any solvent other than starting nitrile or product alcohol (b) with a water immiscible solvent, or (c) with a homogenizing solvent.

The preferred mode of operation depends on the nature of the nitrile being reacted, keeping in mind the necessity of providing adequate water for reductive hydrolysis to occur rather than simple reduction. The main criterion is the ability of the nitrile or product alcohol to dissolve the reactants (nitrile, catalyst, and water) sufficiently to enable reductive hydrolysis to occur.

"Hydrophilic" and some "amphiphilic" nitrile reactants, those which are liquid at reaction temperature and which are sufficiently good solvents for both catalyst and water at the reaction temperature for reductive hydrolysis to occur, are amenable to operation in the neat mode. Similarly, when the product alcohol is a good solvent for the starting nitrile catalyst, and water, the product alcohol itself can be used as the solvent. Lower nitriles such as acetonitrile or propionitrile could thus use the product alcohol as the solvent. Adiponitrile and methylglutaronitrile, though not miscible with water at ambient temperature, become miscible at elevated temperatures, therefore, they can also be considered candidates for operation in the heat mode. Even nitriles which are not completely miscible with water are amenable to the neat mode provided they are capable of dissolving catalyst and sufficient water to favor inductive hydrolysis over simple hydrogenation.

The purpose of using a water-immiscible solvent is to facilitate recovery and recycle of catalyst in the case where the product alcohol is water soluble. This mode is feasible when the nitrile or product alcohol is a sufficiently good solvent for both catalyst and water to favor reductive hydrolysis over simple hydrogenation to amine. The water-soluble product can be separated from the water-insoluble catalyst by simple decantation and/or extraction procedures.

Suitable water-immiscible solvents comprise aliphatic and aromatic hydrocarbons, and water immiscible ethers. Preferred solvents are toluene and t-butyl methyl ether.

The water-immiscible solvent mode is not applicable with hydrophobic nitriles, e.g., dodecanedinitrile or α-methyl benzyl cyanide, due to insufficient contact with water, resulting in hydrogenation to amine rather than reductive hydrolysis.

With hydrophobic nitriles such as dodecanedinitrile or α-methyl benzyl cyanide; a homogenizing solvent is required. This solvent need not be miscible with water, but must be capable of dissolving nitrile, catalyst, and sufficient water to favor reductive hydrolysis over hydrogenation. All the solvents described above for hydrogenation of nitriles to amities can be considered, but the preferred solvents are the lower boiling alcohols and ethers, for example, dimethoxyethane, p-dioxane, tetrahydrofuran (THF), 2-methoxyethanol, 2-ethoxyethanol (Cellosolve®), and 2-butoxyethanol (butyl cellosolve). THF is most preferred.

The amount of catalyst, excess phosphine, temperature, pressure, agitation requirements and sources of hydrogen are the same as discussed above for hydrogenation of nitriles. The pressure employed can be from about 100 kPa (1 atmosphere) to about 15000 kPa. Elevated pressures are preferred since the solubility of hydrogen is increased which leads to higher reactions rates. However, pressures above about 7000 Kpa to about 10000 kPa are generally avoided due to the high cost of equipment capable of operating at such pressures. The preferred pressure is in the range of about 5000 kPa to about 7000 kPa. Preferred catalysts for the reductive hydrolysis process of the present invention comprise those wherein neither $L^3$ is $PR_3$. Most preferred are $RuH_2(H_2)_2(PCy_3)_2$, $RuH_2(N_2)_2(PCy_3)_2$, $RuH_2(H_2)_2(P\text{-}iPr_3)_2$, and $RuH_2(N_2)_2(P\text{-}iPr_3)_2$.

The ruthenium complexes of formula III can also be used as catalysts in a process of the present invention for the selective reductive hydrolysis is of a dinitrile to a hydroxynitrile comprising the steps of contacting the dinitrile with gaseous hydrogen and water in the presence of the catalyst and subsequently agitating the dinitrile, hydrogen, water, and catalyst to form the hydroxynitrile. For example, the major intermediate in the reductive hydrolysis of adiponitrile, 6-hydroxycapronitrile, can be prepared in high yield if the reductive hydrolysis is stopped at an intermediate stage.

The dinitrile can be any linear or branched saturated aliphatic $C_3$ to $C_{19}$ dinitriles and phenyl derivatives thereof, $C_5$ to $C_{14}$ saturated alicyclic dinitriles, $C_7$ to $C_{14}$ aromatic dinitriles. Aliphatic dinitriles comprising about 6 to about 12 carbon atoms are preferred. Preferably, the carbon atoms are arranged in a linear or branched chain. Especially preferred examples of dinitriles are adiponitrile and dodecanedinitrile.

The amount of catalyst, excess phosphine, temperature, solvents and modes of operation, amounts of water, pressure agitation requirements and sources of hydrogen are the same as discussed above for the reductive hydrolysis of nitriles. Preferred catalysts for the selective reductive hydrolysis of a dinitrile comprise those wherein neither $L^3$ is $P_3$. Most preferred are $RuH_2(H_2)_2(PCy_3)_2$, $RuH_2(N_2)_2(PCy_3)_2$, $RuH_2(H_2)_2(P\text{-}iPr_3)_2$, and $RuH_2(N_2)_2(P\text{-}iPr_3)_2$.

The desired product of the selective reductive hydrolysis, a hydroxynitrile, is an intermediate in that variant of the present reductive hydrolysis process which eventually results in the formation of a diol. The hydroxynitrile concentration in the reacting mixture passes through a maximum as the reaction progresses. One objective of this embodiment of the present invention is to maximize the concentration of the hydroxynitrile in the reacting mixture at the highest possible conversion of the starting dinitrile. The yield of the hydroxynitrile and the position of the maximum with respect to dinitrile conversion depend on operating conditions such as temperature, hydrogen pressure, amount and kind of catalyst, dilution of starting dinitrile, as well as, the type of solvent. These variables in turn influence the optimum contact time for the reaction.

The optimum contact time of the present invention needed to favor formation of a hydroxynitrile need be determined only once for any given set of reaction conditions. Once the optimum has been determined, it will remain constant as long as reaction conditions, such as catalyst, reactant concentrations, temperature, and pressure are held constant.

Another embodiment of the present invention is a simple process for separation of the ruthenium complex catalyst from hydrogenation or reductive hydrolysis product compounds and recycle of the catalyst. Conventional methods of accomplishing such separations include fractional distillation, fractional crystallization, chromatography. Distillation methods in particular are very commonly used, where for example, hexamethylenediamine may be separated from the less volatile hydrogenation catalyst by fractional distillation, but the high temperature and subatmospheric pressure required, due to the relatively high boiling point of hexamethylenediamine, may adversely affect catalyst stability.

Unlike most homogeneous catalysts, the catalysts of the present invention are unexpectedly stable inn the presence of water. Therefore, in cases where the product compounds are soluble in water, and where a reaction solvent is employed which is immiscible with water, the product compounds can be separated from the catalyst and reaction solvent by extraction with water. The catalyst is essentially insoluble in water and remains dissolved in the reaction solvent while the water-soluble product compounds are removed into the water extracts. The resulting solution of catalyst in the reaction solvent, which can be dried if desired, is then recycled. The product compounds can be recovered from the water extracts by distillation or any other desired method, without concern for catalyst stability.

Advantages of separation by water extraction comprise simplicity, mild conditions, and low energy consumption. In particular, the extraction can be conducted at mild temperatures, between about 20° C. and about 100° C., and mild pressures, between about 100 kPa and about 500 kPa, which are desirable from the standpoint of maintaining catalyst stability.

EXAMPLES

All manipulations were carried out in a Vacuum Atmospheres glove box (Vacuum Atmospheres Company, Hawthorne, Calif.) with continuous nitrogen purge. Reactions involving hydrogen at pressures of less than 860 kPa were carried out in a 50 mL Fischer-Porter tube. Higher pressure reactions involving hydrogen were carried out in a 50 mL Hastalloy C autoclave (Autoclave Engineers, Erie, Pa.) stirred at 1500 rpm with a gas-inducing turbine blade agitator. Reactor loading and unloading was within the glovebox.

Hydrogenation products were analyzed by gas chromotography using a 0.53 mm internal diameter x 30 m long DB-5 column from J&W Scientific, Folsom, Calif. Infrared spectra were obtained on a Nicolet 205 FTIR spectrometer. NMR spectra were obtained on a GE QE 300 (300 MHz 1H, 121 MHz 31P) spectrometer. Positive H and P shifts were reported as downfield from external TMS or $H_3PO_4$ respectively.

$(COD)RuCl_2$ was prepared according to the method disclosed by M. O. Albers et al., *Inorganic Syntheses*, 1989, 26, 68. Phosphorus ligands were purchased from Strem Chemical Co., Newburyport, Mass., or Aldrich Chemical Co., Milwaukee, Wis. Trimethyisilylmethylmagnesium chloride, $(CH_3)_3SiCH_2MgCl$ and Aliquat 336® are available from Aldrich Chemical Co, Milwaukee, Wis. Petroleum ether, toluene and tetrahydrofuran was purified before use, by distillation from sodium benzophenone.

Abbreviations used throughout are:

| | |
|---|---|
| ACN | aminocapronitrile |
| ADN | adiponitrile |
| BHMT | bis(hexamethylenetriamine) |
| iBu | isobutyl |
| nBu | n-butyl |
| COD | cyclooctadiene |
| COT | cyclooctatriene |
| Cy | cyclohexyl |
| d | doublet |
| Duphos | (-)-1,2-bis((2R,5R)-2,5-dimethylphospholano) benzene |
| Et | ethyl |
| HMD | hexamethylenediamine |
| HMI | hexamethyleneimine (aka azacycloheptane) |
| kPa | kilo Pascals |
| L | any neutral 2-electron donor ligand (comprising $H_2$, $N_2$, and phosphines) |
| m | medium intensity IR band or multiplet NMR lines |
| Me | methyl |
| MGN | 2-methylglutaronitrile |
| N112 | aminocapronitrile |
| $PR_3$ | triorganophosphine (e.g., triphenylphosphine) |
| Ph | phenyl |
| iPr | isopropyl |
| q | quartet |
| s | strong intensity IR band or singlet NMR line |
| t | triplet |
| THA | tetrahydroazapine |

| | |
|---|---|
| THF | tetrahydrofuran |
| Tol | tolyl |
| w | weak intensity IR band |

EXAMPLE 1

A. Preparation and Isolation of $RuH_2(H_2)_2(PCy_3)_2$ from $(COD)RuCl_2$

A mixture of 1.74 g (COD)RuCl$_2$ (6.2 mmol), 3.49 g PCy$_3$ (12.5 mmol), 2.14 g NaOH (54 mmol), 0.0579 g benzyl triethylammonium chloride (0.25 mmol, phase-transfer catalyst), 15 mL toluene, and 5 mL water was stirred under 7000 kPa hydrogen at 40° C. for 7.5 hours. After cooling under hydrogen, the reaction mixture was worked up in a nitrogen-filled glovebox. The solid product was isolated by filtration, washed with 10 mL heptane, and dried under a stream of nitrogen to give 4.0 g pale yellow powder (96% yield). The product was identified by comparison of its $^1H$ and $^{31}P$ NMR to the literature data reported by B. Chaudret et al., Organometallics, 1985, Vol. 4, 1722. $^1H$: 7.85 (t, $J_{PH}$=7.7 Hz). 31P{1H}: 76.9 ppm.

NMR spectra of samples sealed under a hydrogen atmosphere show only $RuH_2(H_2)_2(PCy_3)_2$ while samples prepared under a nitrogen atmosphere showed mixtures of dihydrogen and dinitrogen complexes due to conversion of $RuH_2(H_2)_2(PCy_3)_2$ to $RuH_2(N_2)_2(PCy_3)_2$ as described below. Under a nitrogen atmosphere, both the bis (dihydrogen) and bis(dinitrogen) complexes were generally visible, as well as another species with a singlet in the $^{31}P$ NMR about midway between them. This third species was not identified, but is likely an intermediate in the interconversion of the bis(dinitrogen) and bis(dihydrogen) forms, such as $RuH_2(H_2)(N_2)(PCy_3)_2$ or a five-coordinate species such as $RuH_2(H_2)(PCy_3)_2$ or $RuH_2(N_2)(PCy_3)_2$. Any of these forms, or a mixture, isolated or as prepared in solution, can be Used in hydrogenation reactions.

B. Preparation of $RuH(H_2)_2(PCy_3)$ Solution

A mixture of 0.28 g (COD)RuCl$_2$ (1 mmol), 0.62 g PCy$_3$ (2.2 mmol), 1 mL of 50% aqueous NaOH, 0.0553 g benzyl triethylammonium chloride (0.24 mmol, phase-transfer catalyst), and 15 ml benzene was stirred under 860 kPa hydrogen at 60° C. for 18 hours. After cooling under hydrogen, the reaction mixture was worked up in a nitrogen-filled glovebox. After separating the benzene phase, the aqueous phase was washed with 3 mL benzene, which was combined with the benzene phase removed earlier. NMR spectra the resulting benzene solution showed the presence of $RuH_2(Hd)_2(PCy_3)_2$ as well as $RuHZ(N_2)_2(PCy_3)_2$, which formed during workup of the reaction mixture under nitrogen. This benzene solution was used for the hydrogenation in Example 35 without further treatment.

EXAMPLE 2

Valeronitrile Hydrogenation Using $RuH_2(H_2)(PCy_3)_2$

A mixture of 0.065 g RuHi(H$_2$)$_2$(PCy$_3$)$_2$ (0.1 mmol, prepared as in Example 31A above), 0.3914 g valeronitrile (4.71 mmol), and 0.21 g t-butylbenzene (internal standard) in 27.3 g toluene was hydrogenated at 60° C. and 450 kPa H$_2$ for 22 hours. GC analysis showed complete conversion of valeronitrile, with n-amylamine the only detected product.

EXAMPLE 3

ADN Hydrogenation Using $RuH_2(H_2)_2(PCy_3)_2$ in Toluene

Figure 2:
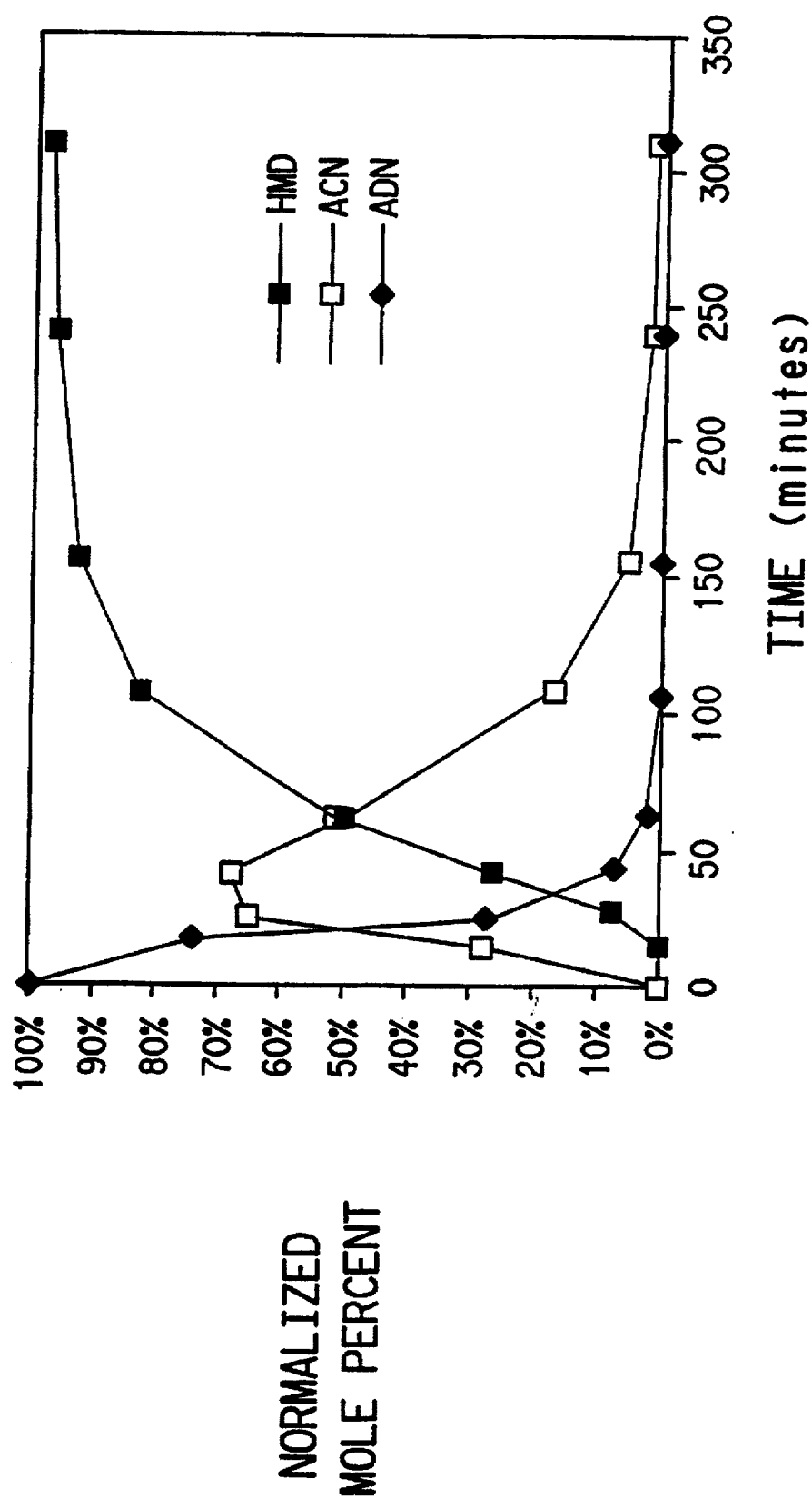
FIG. 2 is a graph comparing adiponitrile (ADN) consumption, aminocapro-nitrile (ACN) formation and hexamethylenediamine (HMD) formation as a function time for the catalyst of Example 3.

A mixture of 0.0737 g RuH$_2$(H$_2$)$_2$(PCy$_3$)$_2$ (0.1 mmol) and 0.5155 g ADN (4.77 mmol) in 28.89 g toluene was hydrogenated at 90° C. under 7000 kPa H$_2$. The reaction was sampled periodically and analyzed by gc, with the results shown graphically in FIG. 2. This experiment illustrates several key advantages of this catalyst. First, reaction is rapid, and the ultimate yield of HMD is very high. After 5 hours, ADN conversion is complete with the HMD yield >97%. Further, selectivity to ACN at intermediate ADN conversions is much higher than that expected statistically (see FIG. 1). Even at 93% ADN conversion, ACN selectivity is still 72% vs 45% predicted statistically.

EXAMPLE 4

ADN Hydrogenation Using $RuH_2(H_2)_2(PCy_3)_2$ in Tetrahydrofuran

A mixture of 0.0656 g RuH$_2$(H$_2$)$_2$(PCy$_3$)$_2$ (0.1 mmol), 2.7584 g ADN (25.5 mmol), and 2.76 g t-butylbenzene (internal standard) in 25.84 g THF was hydrogenated at 100° C. under 7000 kPa H$_2$. After 16.5 hours, ADN conversion was complete and the HMD yield was 99%. ACN selectivity at 94% ADN conversion was 71%, similar to that obtained in toluene solvent (see Example 3 above).

EXAMPLE 5

ADN Hydrogenation Using $RuH_2(H_2)_2(PCy_3)_2$ in HMD/NH$_3$

A mixture of 0.0710 g RuH$_2$(H$_2$)$_2$(PCy$_3$)$_2$ (0.1 mmol), 7.8052 g ADN (72.2 mmol), 0.6643 g PCy$_3$, and 6 mL ammonia in 18.16 g HMD was hydrogenated at 70° C., adding enough .hydrogen to bring the total system pressure up to 7000 kPa at reaction temperature. After 16.5 hours, the reaction was stopped and analyzed by GC, with the results shown in Table I below (excluding HMD charged as solvent). The catalyst was clearly active in the presence of ammonia, as evidenced by the 97% ADN conversion attained. Conversion of ACN to HMD was still incomplete due to the very high ADN/RuH$_2$(H$_2$)$_2$(PCy$_3$)$_2$ ratio (>700/1) in this example.

TABLE I

| Final Composition by GC | |
|---|---|
| Component | Normalized Mole Percent |
| HMI | 0.19 |
| THA | 10.78 |
| ADN | 3.06 |
| ACN | 52.44 |
| HMD | 33.49 |
| BHMT | 0.04 |

EXAMPLE 6

ADN Hydrogenation with $RuH_2(H_2)_2(PCy_3)_2$ at 80° C.

A mixture of 0.1 mmol catalyst; 4.62mmol ADN, and 35 mL toluene was heated to 80° C. in a stirred 50 cc autoclave under 7000 kPa H$_2$. Samples were withdrawn periodically and analyzed by gc. After 8.4 hours, the ADN conversion was >99%. The composition was 6% ACN and 94% HMD.

EXAMPLE 7

2-Methylglutaronitrile (MGN) Hydrogenation Using RuH$_2$(H$_2$)(PCy$_3$)$_2$ A mixture of 0.027 mmol catalyst, 4.92 mmol MGN, and 35 mL toluene was heated to 90° C. in a stirred autoclave under 7000 kPa H$_2$. Samples were withdrawn periodically and analyzed by gc. After 2.5 hours, the MGN was completely hydrogenated. The yield of 2-methyl-1,5-pentane diamine was 96%.

EXAMPLE 8

ADN Hydrogenation and Recycle of RuH$_2$(H$_2$)$_2$(PCy$_3$)$_2$

This example demonstrates recycle of catalyst by aqueous/organic extraction. HMD is very soluble in water while the catalyst and phosphine ligands are not, so the catalyst and products are easily separated by water extraction. The catalysts of the present invention are remarkably stable toward water; unlike many organometallic hydrides which decompose on contact with water, releasing hydrogen gas.

A mixture of 0.1 mmol RuH$_2$(H$_2$)$_2$(PCy$_3$)$_2$, 5.27 mmol ADN, and 35 mL toulene was heated in a stirred autoclave to 100° C. under 7000kPa H$_2$. After 4.3 h, the reaction was brought into the glovebox extracted in series with two mL potions of water. Analysis of the combined water extracts showed the presence of 4.49 mmol HMD. 85% of the theoretical amount.

The toluene phase was returned to the autoclave and an additional 6.46 mmol, ADN was added. The mixture was again heated to 100° C. under 7000 kPa H$_2$. After 5.7 hours, workup by water extraction as before and analysis of the water phase showed the presence of 5.17 mmol HMD, 80% of the theoretical amount.

EXAMPLE 9

Undecyl Cyanide Hydrogenation with RuH$_2$(H$_2$)$_2$(PCy$_3$)$_2$

A mixture of 0.1089 mmol catalyst, 5.54 mmol C$_{11}$H$_{23}$CN, and 35 mL toluene was heated to 100° C. in a stirred autoclave under 7000 kPa H$_2$. Samples were withdrawn periodically and analyzed by gc. After 1.6 hours, the composition was 5% unconverted undecyl cyanide and 95% dodecyl amine.

EXAMPLE 10

Valeronitrile hydrogenation with RuH$_2$(H$_2$)$_2$(PCy$_3$)$_2$ at 1 atm H$_2$ and 25° C.

A mixture of 0.0861 mmol catalyst, 4.281 mmol valeronitrile, 0.2130 g t-butylbenzene(internal standard for go analysis), and 10.2 g toluene was stirred at room temperature ($\approx$25° C.) while hydrogen was bubbled through the solution. After 48 hours, gc analysis showed that the valeronitrile had been quantitatively converted to amylamine.

This example showed that the catalyst is active even under very mild conditions and produces very high yields of primary amines in comparison. hydrogenation of valeronitrile using Raney metal catalysts typically require elevated temperatures and pressures and produce only 75–85% yields of pentylamine. Addition of NH$_3$ is required to achieve yields >90% (M. Besson et al., Bull. Chem. Soc.Fr., 1990, 127, 5).

EXAMPLE 11

Preparation of RuH$_2$(N$_2$)$_2$(PCy$_3$)$_2$

A mixture of 2.3 g RuH$_2$(H$_2$)$_2$(PCy$_3$)$_2$ (3.44 mmol) and 53 g toluene was stirred and sparged with nitrogen gas for 5 minutes. The mixture was filtered, and the filtrate evaporated to dryness under a rapid stream of nitrogen gas. The resulting solid was rinsed with 5 mL petroleum ether and dried under nitrogen to give 1.5 g product. Since the spectroscopic data for this compound did not match any of the known classes of ruthenium hydrides, the crystal structure was determined (see below) showing the product to be RuH$_2$(N$_2$)$_2$(PCy$_3$)$_2$.

The NMR and IR spectra were very distinctive. In addition to the expected cyclohexyl protons, the $^1$H spectrum showed one triplet hydride at −12.8 ppm. The P-H coupling constant(20 Hz) matched that seen in the proton-coupled $^{31}$P NMR spectrum, which showed a triplet at 60.5 ppm. Appearance of these two triplets was clearly consistent with a RuH$_2$P$_2$ core. The IR spectrum showed very strong bands due to the dinitrogen ligands at 2121 and 2161 cm$^{-1}$ and a weak hydride band at about 1899 cm$^{-1}$.

NMR spectra showed that, under hydrogen, solutions of the bis(dinitrogen) complex very rapidly convered to RuH$_2$(H$_2$)$_2$(PCy$_3$)2. This process was readily reversible by reexposure to nitrogen gas.

A sample of RuH$_2$(N$_2$)$_2$(PCy$_3$)$_2$ was recrystallized by extraction with petroleum ether at 25° C., filtration, and slow evaporation of the filtrate. An x-ray structure was determined, and the two hydride ligands were located.

EXAMPLE 12

ADN Hydrogenation Using RuH$_2$(N$_2$)$_2$(PCy$_3$)$_2$

A mixture of 0.0709 g RuH$_2$(N$_2$)$_2$PCy$_3$)$_2$ (0.0985 mmol) and 2.9905 g ADN (27.6 mmol) in 26.38 g 2-methylpentamethylenediamine was hydrogenated at 100° C. and 7000 kPa H$_2$. After 1 hour, the composition was 9% ADN, 64% ACN, and 27% HMD. After 3.4 hours, the ADN was completely hydrogenated, with HMD being the only detected product.

EXAMPLE 13

Preparation of RuH$_2$(N$_2$)$_2$(P-iPr$_3$)$_2$

A mixture of 0.42 g (COD)RuCl$_2$ (1.5 mmol), 0.5070 g P-iPr$_3$ (3.16 mmol), 0.2950 g NaOH (7.4 mmol), 0.03 g benzyltriethylammonium chloride (0.13 mmol), 5 mL water and 5 mL toluene was stirred for 23.5 hours at 20° C. under 860 kPa H$_2$. The resulting mixture was filtered, then the toluene phase was separated from the filtrate and washed with 5 mL water. The toluene was removed under a stream of nitrogen gas, and the resulting brown solid washed with methanol, collected by filtration; and dried under a stream of nitrogen. Yield: 0.36 g (50%). Spectroscopic data show the product to be RuH$_2$(N$_2$)$_2$(P-iPr$_3$)$_2$, apparently isostructural with the PCy$_3$ complex described above. $^{31}$P$\{^1$H$\}$: 71.4 (s); $^1$H: −13.8 (br); IR: 2133, 2125 cm$^{-1}$ ($v_{NN}$)

EXAMPLE 14

Preparation of RuH$_2$(H$_2$)$_2$(P-iPr$_3$)$_2$

A sample of the dinitrogen complex described above was dissolved in deuterobenzene and sealed in an NMR tube under 1 atmosphere H$_2$. NMR spectra showed the dinitrogen complex was completely and cleanly converted to RuH$_2$(H$_2$)$_2$(P-iPr$_3$)$_2$. The $^1$H NMR was especially diagnostic of the indicated structure, revealing a hydride triplet at −8.1 ppm (J$_{PH}$ about 8 Hz) and the correct integrated intensities for 2 phosphine ligands and 6 hydrides. $^{31}$P {$^1$H}: 88.9 (s).

EXAMPLE 15

ADN Hydrogenation Using RuH$_2$(N$_2$)$_2$(P-iPr$_3$)$_2$

A mixture of 0.0441 g RuH$_2$(N$_2$)$_2$(P-iPr$_3$)$_2$ (0.1 mmol) and 2.77 g ADN (25.62 mmol) in 27.45 g toluene was hydrogenareal at 100° C. and 7000 kPa H$_2$. After 1 hour, the composition was 46% ADN, 52% ACN, and 3% HMD. After 20.4 hours, the ADN was completely converted to a mixture of 99% HMD and 1% HMI.

EXAMPLE 16

Preparation of RuH$_2$(H$_2$)(PPh$_3$)$_3$ and RuH$_2$(N$_2$)(PPh$_3$)$_3$

A mixture of 0.42 g (COD)RuCl$_2$ (1.5 mmol), 1.26 g PPh$_3$ (4.80 mmol), 0.46 g NaOH (11.5 mmol), 0.027 g benzyltriethylammonium chloride (0.118 mmol), 5 mL water and 5 mL toluene was stirred for 27.5 hours at 20° C. under 860 kPA H$_2$. The reaction. Was brought into a nitrogen-filled glovebox, where the yellow precipitate was collected by filtration, rinsed with several potions of petroleum ether, and dried, first under a stream of nitrogen, then in vacuo. Yield 1.07 g (about 78%).

Comparison of IR and NMR spectra to the literature reported by D. E. Linnet al., *J Am. Chem. Soc.*; 1987, Vol. 109, 2969, indicated the product to be a mixture of RuH$_2$(N$_2$i(PPh$_3$)$_3$, and RuH$_2$(H$_2$)(PPh$_3$)$_3$. The hydrogenation procedure produced RuH$_2$(H$_2$i(PPh$_3$)$_3$, but the exact proportions of dihydrogen and dinitrogen complexes observed depended on the extent of nitrogen exposure during workup aid sample preparation, consistent with the known easy interconversion of these complexes.. As described above for RuH$_2$(H$_2$)$_2$(PCy$_3$)$_2$, clean spectra RuH$_2$(H$_2$)(PPh3)$_3$ could only be obtained on samples under a hydrogen atmosphere. Obviously, either form can be used in a hydrogenation reaction, since under hydrogen both produce RuH$_2$(H$_2$)(PPh$_3$)$_3$.

EXAMPLE 17

ADN Hydrogenation Using RuH$_2$(H$_2$)(PPh$_3$)$_3$

A mixture of 0.0886 g RuH$_2$(H$_2$)(PPh$_3$)$_3$ (0.1 mmol) and 2.8071 g ADN (26 mmol) in 28.7 g toluene was hydrogenated at 100° C. and 7000 kPa H$_2$. After 1 hour, the composition was 67% ADN, 30% ACN, and 3% HMI. After 6 hours, the composition was 2% ADN,66% ACN, 30% HMD, and 2% HMI.

EXAMPLE 18

ADN Hydrogenation with RuH$_2$(H$_2$)(PPh$_3$)$_3$

A mixture of 0.1 mmol catalyst, 10.5 mmol ADN, and 35 mL toluene was heated to 80° C. in a stirred autoclave under 7000 kPa H$_2$. Samples were withdrawn periodically and analyzed by gc. After 22.1 hours, the ADN conversion was 98%. The composition was 2% ADN, 28% ACN, 70% HMD, and 1% others.

EXAMPLE 19

Preparation of RuH$_2$(H$_2$)(P benzyl$_3$)$_3$

A mixture or 0.43 g (COD)RuCl$_2$ (1.5 mmol), 1.83 g tribenzylphosphine (6.01 mmol), 0.49 g NaOH (12.3 mmol), 0.033 g benzyltriethylammonium chloride (0.144 mmol), 5 mL water, and 5 mL toluene was stirred at 25° C. under 860 kPa H$_2$ for 20.75 hours. The product, which precipitated as an off-white solid, was collected by filtration, rinsed with 10 mL methanol, and dried under a stream of nitrogen. Yield: 1.42 g (90% yield). This catalyst was identified from its nmr spectra, which were similar to those of other RuH$_2$(H$_2$)(PR$_3$)$_3$ complexes, (e.g., Example 16) and by its reaction with N$_2$ to give RuH$_2$(N$_2$)(P benzyl$_3$)$_3$. $^1$H: −9.03 (s); $^{31}$P {1H}: 43.5 (s).

EXAMPLE 20

ADN Hydrogenation using RuH$_2$(H$_2$)(P benzyl$_3$)$_3$

A mixture of 0.0739 g RuH$_2$(H$_2$)(P benzyl$_3$)$_3$ (0.1 mmol) and 2.79 g ADN in 27.8 g toluene was hydrogenated at 100° C. and 7000 kPa H$_2$. After 1 hour, the composition was 45% ADN, 53% ACN, and 2% HMD. After 2.5 hours, all ADN had been hydrogenated to a mixture of 95% HMD, 2% ACN, and 3% HMI.

EXAMPLE 21

Preparation of RuH$_2$(H$_2$(P-iBu$_3$)$_3$

A mixture of 0.4288 g (COD)RuCl$_2$, (1.53 mmol), 1.03 g P-iBu$_3$ (5.09 mmol), 0.28 g NaOH (7.0 mmol), 0.0318 g benzyltriethylammonium chloride (0.139 mmol), 5 mL water and 5 mL toluene was stirred at 20° C. under 860 kPa H$_2$ for 19.5 hours. The toluene phase was separated and stripped down to dryness in vacuo. The residue was extracted with 10 mL petroleum ether, and the extracts stripped down to dryness. Trituration with methanol gave an orange solid. Yield: 0.65 g (60%). This catalyst was identified from its nmr spectra, which were similar to those of other RuH$_2$(N$_2$)(PR$_3$)$_2$ complexes, (e.g., Example 16) and by its reaction with N$_2$ to give RuH$_2$(H$_2$)(P-iBu$_3$)$_3$. $^1$H: −8.5 (q, J$_{PH}$=6Hz); $^{31}$P{$^1$H}: 39.8 (s).

EXAMPLE 22

ADN Hydrogenation Using RuH$_2$(H$_2$)(P-iBu$_3$)$_3$

A mixture of 0.079 g RuH$_2$(H$_2$)(P-iBu$_3$)$_3$ (0.1 mmol) and 3.0526 g ADN (28.24 mmol) in 27.76 g toluene was hydrogenated at 100° C. and 7000 kPa H$_2$. After 1 hour, the composition was 19% ADN, 65% ACN, and 12% HMD. This corresponded to an ACN selectivity of 84% at 81% ADN conversion, vs 61% expected statistically.

EXAMPLE 23

Preparation of RuH$_2$(H$_2$)(Cy$_2$PCH$_2$CH$_2$OCH$_3$)$_3$ and RuH$_2$(N$_2$)(Cy$_2$PCHICH$_2$OCH$_3$)$_3$ A mixture of 1.55 mmol (COD)RuCl$_2$, 3.1 mmol Cy$_2$PCH$_2$CH$_2$OCH$_3$ (prepared according to E. Lindner et al., *J. Organomet. Chem.*, 1987, Vol. 335, p. 59), 7.96 mmol NaOH, 0.067 mmol [Et$_3$NBenzyl]Cl, 5 ml toluene, and 5 ml water was stirred in a Fisher-Porter tube at 25° C. under 860 kPa H$_2$ for 24 hours. The mixture was filtered, the toluene phase was separated, and the toluene removed in vacuo. The residue was extracted with diethyl ether and the ether removed to dryness to yield 0.8974 g (64% yield .based on Ru, 100% yield based on phosphine) RuH$_2$(N$_2$)(Cy$_2$PCH$_2$CH$_2$OCH$_3$)$_3$, identified spectroscopically by NMR and IR. NMR: $^{31}$P{$^1$H}: 41.8 (d, 2P, JPP E 16 Hz), 32.3 (t, 1P). $^1$H: −10.8 (dt, 1H), −14.5 (m, 1H). Under hydrogen, this dinitrogen complex converted to the dihydrogen form. $RuH_2(H_2)(Cy_2PCH_2CH_2OCH_3)_3$: $^{31}P\{^1H\}$: 50.5 ppm (s). $^1H$: 9.16 (s).

EXAMPLE 24

ADN hydrogenation using $RuH_2(H_2)(Cy_2PCH_2CH_2OCH_3)_3$

A solution of 0.1 mmol catalyst and 5.1 mmol ADN in 35 ml 2-methyl-1,5-diaminopentane was charged to a Fisher-Porter tube and heated under 860 kPa $H_2$ to 100° C. After 3 hours, gc analysis showed complete conversion of the ADN and a 93% yield of HMD.

EXAMPLE 25

Preparation of $RuH_2(P-nBu_3)_4$

A mixture of 0.28 g $(COD)RuCl_2$ (1.0 mmol), 0.81 g P-iBu$_3$ (4.0 mmol), 0.040 g benzyltriethylammonium chloride (0.175 mmol), 1 mL 50% aqueous NaOH (12.5 mmol), and 15 mL toluene was stirred at 60° C. under 860 kPa $H_2$. The toluene phase was separated and evaporated to dryness in vacuo. IR and $^1H$ nmr data agreed with that reported by T. Mitsudo et al., in *J. Org. Chem.*, 1985, Vol. 50, 565. NMR spectra indicated a 75% yield of $RuH_2(P-nBu_3)_4$.

EXAMPLE 26

Preparation of $RuH_2(dppb)_2$

A mixture of 0.28 g $(COD)RuCl_2$ (1.0 mmol), 0.91 g 1,4-bis(diphenyl-phosphino) butane (dppb, 2.1 mmol), 0.31 g NaOH (7.8 mmol), 0.03 g benzyltri-ethylammonium chloride (0.131 mmol), 5 mL water and 5 mL toluene were stirred at 50° C. under 860 kPa. $H_2$ for 20.5 hours. The product precipitated as an off-white solid. It was collected by filtration, rinsed with petroleum ether, and dried under nitrogen. Yield: 0.8 g (84%).

NMR spectra showed a $RuH_2P_4$ pattern, clearly identifying the product as $RuH_2(dppb)_2$, previously reported by T. V. Ashworth et al., in *Chem. Comm.*, 1976, 705. $^1H$: −9.6 (m), $^{31}P\{^1H\}$: 50.1 (br, 2P), 35.6 (br, 2P).

EXAMPLE 27

Preparation of Propionitrile Complex

A mixture of 0.6954 g $RuH_2(H_2)_2(PCy_3)_2$ (1.04 mmol) and 0.2948 g propionitrile (5.35 mmol) in 5.76 g toluene was stirred for 5 minutes. The toluene was removed in vacuo and the resulting solid washed with pet ether, then dried in vacuo. Yield: 0.6 g white powder. $^{31}P\{^1H\}$: 61.54 ppm(s). $^1H$: two hydride multiplets at −12.5 and −15.5 ppm. IR: $v_{CN}$ at 2205, 2221 cm$^{-1}$, $v_{NN}$ at 2097, $v_{RuH}$ at 1943 (br). The spectroscopic data suggest a cis-dihydride, $RuH_2(N_2)(CH_3CH_2CN)(PCy_3)_2$, containing trans- phosphines.

EXAMPLE 28

ADN Hydrogenation Using Propionitrile Complex

A solution of 0.0786 g (0.1 mmol) propionitrile complex and 2.84 g ADN (26 mmol) in 26.93 g toulene was heated to 100° C. under 7000 kPa $H_2$. After 1 hour, the normalized composition was 59% ADN, 40% N112, 1% HMD. This is essentially equivalent to a comparable hydrogenation using $RuH_2(H_2)_2PCy_3)_2$ as shown by Example 29 below.

EXAMPLE 29

ADN Hydrogenation Using $RuH_2(H_2)_2(PCy_3)_2$

In a separate experiment, a solution of 0.1 mmol $RuH_2(H_2)_2(PCy_3)_2$ and 2.73 g ADN (25.3 mmol) in 27.77 g toluene was hydrogenated under the same conditions as used above. After 1 hour, the normalized composition was 49% ADN, 49% ACN, 2% HMDL.

EXAMPLE 30

Preparation of Adiponitrile Complex

A mixture of 0.2956 g $RuH_2(H_2)_2(PCy_3)_2$ (0.44 mmol) and 0.0452 g ADN (0.42 mmol) in 0.7082 g toluene was stirred at 20° C. for 72 hours. Addition of 5 mL petroleum ether caused immediate precipitation of the product, which was collected and dried. The crude product was characterized spectroscopically and used without purification for a hydrogenation (see below). Tentative assignment of key IR bands: 2190 ($v_{C\equiv N}$), 2051 ($v_{N\equiv N}$), and 1565 cm$^{-1}$ (possible $v_{N=C}$) as well as a broad band centered on 1940 cm$^{-1}$ ($v_{RuH}$). $^1H$: broad weak hydride ≈12 ppm. $^{31}P\{^1H\}$:: broad bands ≈38, 52, and 75 ppm in addition to ≈20% free $PCy_3$ at 10.5 ppm.

EXAMPLE 31

ADN Hydrogenation Using Adiponitrile Complex

A mixture of the ADN complex described above (0.079 g, ≈0.1 mmol) and 2.735 g ADN (25.3 mmol) in 27.79 g toluene was hydrogenated at 100° C. and 7000 kPa $H_2$. After 1 hour the composition was 27% ADN, 65% ACN, and 8% HMD.

EXAMPLE 32

Preparation of Acetonitrile Complex

A mixture of 0.25 g $RuH_2(H_2)_2(PCy_3)_2$ (0.374 mmol), 1 g $CH_3CN$ (24.2 mmol), and 1 g toluene Was stirred for 5 days. The white precipitate was separated and rinsed with ether, then dried in vacuo. The crude product was characterized spectroscopically and used in hydrogenations without purification. Tentative assignments: $^{31}P\{^1H\}$: 62.2 (s). $^1H$: Hydrides at −13.1 (m), −16.3 (m). IR: 2224, 2211 ($v_{CN}$), 2097 ($v_{NN}$), 1833, 1879, 1922, 1959 ($v_{RuH}$), 1578 ($v_{C=N}$).

EXAMPLE 33

Preparation of $RuH_2(PCy_3)_2$ (o-benzoquinone diimine)

A mixture of 0.41 g $RuH_2(N_2)_2(PCy_3)_2$ (0.57 mmol) and 0.083 g 1,2-diaminobenzene (0.77 mmol) in 5.1 g tetrahydrofuran was heated briefly to reflux (2 minutes) to give a dark orange solution. After cooling and stirring for 3.5 hours, the solution was stripped down to dryness in vacuo, giving a red tar. Trituration with petroleum ether gave an orange powder, which was collected and dried in vacuo. Yield: 0.36 g (82%). $^1H$: hydride at −10.0 ($J_{PH}$=36 Hz, 2H), cyclohexyl protons at 1–2 ppm (m, 66H), aromatic protons at 6.5, 6.9 ppm (m, 4H), and imine protons at 8 ppm (br, 2H). $^{31}P$: 84.7 ppm (singlet when proton decoupled or triplet with proton coupling, $J_{PH}$=36 Hz). IR (KBr): $v_{NH}$ at 3365 (w), and 3386 (w)cm$^{-1}$: 1997(s), 2049(m) ($v_{RuH}$). The $^1H$ nmr and IR data are similar to that reported for other o-benzoquinone diimine complexes (see for example A. Anillo et al., *J. Chem. Soc., Dalton Trans.*, 1993, 1125 and references therein).

EXAMPLE 34

ADN Hydrogenation Using $RuH_2(PCy_3)_2$ (o-benzoquinone diimine) as Catalyst A solution of 0.065 g catalyst (0.08 mmol) and 0.97 g ADN (8.98 mmol) in 35 mL THF was charged to a 50 cc Fisher-porter tube, pressurized with 860 kPa $H_2$, and heated to 80° C. After 4.3 hours, the normalized composition was 36% ADN, 58% ACN, and 6% HMD, indicating 91% ACN selectivity at 64% ADN conversion vs 75% expected statistically. After 21 hours, all the ADN was hydrogenated to a mixture of 1% ACN, 82% HMD, and 7% THA, and 9% HMI.

EXAMPLE 35

Selective Hydrogenation of Adiponitrile (ADN) to Aminocapronitrile (ACN) Using $RuH_2(H_2)_2(PCy_3)_2$ A mixture of 0.1 mmol $RuH_2(H_2)_2(PCy_3)_2$ (in 3.3 g benzene solution) prepared as in Example 1B, 0.31 mmol $PCy_3$, 4.8 mmol ADN, and 0.11 g cyclododecane (internal standard for gc analysis) in 35 mL toluene was heated in a stirred autoclave to 80° C. under 7000 kPa $H_2$. After 1.5 hours, the ADN conversion was 99%. The yields of ACN and HMD were 83% and 15%, respectively. The ACN selectivity is thus 84% at 99% ADN Conversion.

FIG. 1 shows that the ACN selectivity achieved using conventional Raney Ni closely follows the calculated statistical curve for ACN selectivity. In contrast, the 85% ACN selectivity achieved in this example at 99% ADN conversion is much higher than the 17% selectivity expected statistically at this conversion.

This hydrogenation was continued to demonstrate complete hydrogenation and showed that the catalyst was still active. After 8 h, the ADN conversion was >99% and the yield of HMD was 85%.

EXAMPLE 36

MGN Reductive Hydrolysis Using $RuH_2(H_2)_2(PCy_3)_2$

A mixture of 0.1 mmol catalyst (in 3.5 g toluene solution), 5.47 mmol MGN, 14 g THF, 16 g water, and 0.1115 g cyclododecane (internal standard for gc analysis) was stirred in an autoclave and heated to 80° C. under 7000 kPa $H_2$. After 3.5 h, the MGN was completely converted and the yield of 2-methylpentanediol was 70%.

COMPARATIVE EXAMPLE A

Comparative ADN Hydrogenation Using $RuH_2(P-nBu_3)_4$

A mixture of 0.0700 g $RuH_2(P-nBu_3)_4$ (0.1 mmol) and 0.5378 g ADN (4.98 mmol) in 29.6 g toluene was hydrogenated at 90° C. and 7000 kPa $H_2$. After 7.3 hours, approximately 6% of the ADN had been hydrogenated, showing that this is an active catalyst, though very slow compared to the preferred catalyst of Example 3.

COMPARATIVE EXAMPLE B

ADN Hydrogenation Using $RuH_2(dppb)_2$

A solution of 0.1253 g (0.13 mmol) $RuH_2(dppb)_2$, 3.53-g (32.67 mmol) ADN. in 27.03 g 2-methyl-1,5-diaminopentane was heated to 100° C. under 7000 kPa $H_2$. After 3.1 hours, gc analysis showed that 25% ADN had been converted. However, CPI was the main product, with only about 1% each of ACN and HMD detected. A similar hydrogenation using our preferred catalyst in Example 12 resulted in essentially complete conversion of ADN to HMD.

COMPARATIVE EXAMPLE C

ADN Hydrogenation with $K[RuH_3(PPh_3)_3]$ in Toluene

A mixture of 0.1 mmol $K[RuH_3(PPh_3)_3]$, 10 mmol ADN, 70 mL toluene, and 5–6 mL THF (to facilitate dissolution) was heated to 80° C. in a stirred autoclave under 7000 kPa $H_2$. Samples were withdrawn at 1 hour intervals and analyzed by gc. After 14 hours, no hydrogenation was observed; the complex was completely inactive.

COMPARATIVE EXAMPLE D

ADN Hydrogenation with $K[RuH_3(PPh_3)_3]$ in DMF

Since DMF is more polar than toluene, it was thought that it could be a better solvent for charged species such as $K[RuH_3(PPh_3)_3]$ and provide higher activity.

A mixture of 0.1 mmol $K[RuH_3(PPh_3)_3]$, 10 mmol ADN, and 35 mL DMF was heated to 80° C. in a Fisher-Porter tube under 860 kPa $H_2$. Samples were withdrawn periodically and analyzed by gc. After 6 hours, about 17% of the ADN had been converted, but the dominant product was 2-cyanocyclopentylimine (CPI) (77% selectivity). CPI formation is a known, base-catalyzed, reaction of ADN, so $K[RuH_3(PPh_3)_3]$ was clearly acting primarily as a strong base rather than as a hydrogenation catalyst.

COMPARATIVE EXAMPLE E

ADN Hydrogenation with $K[Ru_2H_6PPh_3)_6]$

A mixture of 0.074 g $K[Ru_2H_6(PPh_3)_6]$ (0.081 mmol Ru), 10 mmol ADN, and 70 mL toluene was heated to 80° C. under 7000 kPa $H_2$. Samples were withdrawn at 1 hour intervals and analyzed by go. After 13 hours, the ADN conversion was 98%. The composition was 2% ADN, 45% ACN, 52% HMD, and 1% others.

Comparison of this hydrogenation to a similar run using $RuH_2(H_2)(PPh_3)_3$ showed that $K[Ru_2H_6(PPh_3)_6]$ had a faster initial ADN hydrogenation rate, but as the run proceeded, either catalyst deactivation or a slower ACN hydrogenation rate resulted in similar overall performance for formation of HMD. See Table II below.

TABLE II

| Catalyst | $RuH_2(H_2)(PPh_3)_3$ | $K[Ru_2H_6(PPh_3)_6]$ |
|---|---|---|
| Time to reach 50% ADN conversion | 170 min. | 65 min. |
| Time to reach 50% HMD formation | 970 min. | 730 min. |

COMPARATIVE EXAMPLE F

ADN Hydrogenation with $K[Ru_2H_6(PPh_3)_6]$

A mixture of 0.0952 g $K[Ru_2H_6(PPh_3)_6]$ (0.104 mmol Ru), 5.34 mmol ADN, and 35 mL toluene was heated to 80° C. in a stirred autoclave under 7000 kPa $H_2$. Samples were withdrawn periodically and analyzed by gc. After 7.5 hours, the ADN conversion was 94%. The composition was 6% ADN, 67% ACN, 22% HMD, and 5% others. FIG. 3 is a graph comparing HMD formation as a function of time for the preferred catalyst of Example 6 and the catalyst of this example, run under similar conditions.

What is claimed is:

1. A process for the preparation of a ruthenium complex of the formula $RuH_2L_2(PR_3)_2$, wherein:

$PR_3$ represents a phosphine ligand, wherein
   each R is a substituent independently selected from the group consisting of H, a hydrocarbyl group, and an assembly of at least two hydrocarbyl groups connected by ether or amine linkages; and
   each L is a ligand independently selected from $H_2$ or an additional equivalent of the phosphine ligand $PR_3$;
   each phosphine ligand is present as a separate ligand or cojoined with at least one other phosphine ligand, comprising the steps of:
   (a) contacting a ruthenium compound of the formula $R^1_2RuX_2$, wherein $R^1$ is a mono- or poly-, cyclic- or acyclic alkene ligand, present as either two separate ligands or as a single polyalkene ligand and X is a halide or a pseudohalogen, and $PR_3$ with gaseous hydrogen in the presence of water, a strong base, an organic solvent, and a phase transfer catalyst to form a biphasic medium;
   (b) agitating the medium; and
   (c) separating the organic phase comprising the ruthenium complex from the aqueous phase, and optionally isolating the ruthenium complex from the organic solvent.

2. The process of claim 1 wherein the ruthenium compound, $R^1_2RuX_2$, is selected from the group consisting of: (norbornadiene)$RuCl_2$, (cyclohexadiene)$RuCl_2$, (cycloheptatriene)$RuCl_2$, and (1,5-cyclooctadiene)$RuCl_2$.

3. The process of claim 1 wherein each R is a cyclohexyl group.

4. The process of claim 1 wherein at least one L ligand is $H_2$ and further comprising adding nitrogen to the medium after step (b) or to the product optionally isolated in step (c) to yield a ruthenium complex having the formula $RuH_2(N_2)(PR_3)_3$ or $RuH_2(N_2)_2(PR_3)_2$.

5. A process for the hydrogenation of an organic nitrile, comprising the steps of:
   (a) contacting said nitrile with gaseous hydrogen in the presence of a ruthenium complex catalyst having the formula $RuH_2L^3_2(PR_3)_2$, wherein:
   $PR_3$ is a phosphine ligand, wherein
   each R is a substituent independently selected from the group consisting of: H, a hydrocarbyl group, and an assembly of at least two hydrocarbyl groups connected by ether or an amine linkages; and
   each $L^3$ is a ligand independently selected from the group consisting of: $H_2$, $N_2$, $R^2CN$, and an additional equivalent of the $PR_3$ phosphine ligand, provided both $L^3$ are not PR3;
   $R_2$ is a hydrocarbyl group;
   wherein each phosphine ligand is present as a separate ligand or cojoined with at least one other phosphine ligand; and
   (b) subsequently agitating the nitrile, hydrogen and catalyst to form a primary amine.

6. The process of claim 5 wherein contact is made at a temperature of about 0° C. to about 200° C. at a pressure of about 100 kPa to about 15000 kPa, optionally in the presence of a solvent.

7. The process of claim 6 wherein the primary amine is water-soluble and wherein the solvent is immiscible with water, further comprising separating the primary amine by extraction with water from the solvent and the catalyst.

8. The process of claim 5 wherein the nitrite is selected from the group consisting of: adiponitrile, 2-methylglutaronitrile, valeronitrile and dodecanedinitrile.

9. The process of claim 5 wherein the nitrile is a dinitrile and the primary amine is a diamine.

10. The process of claim 5 wherein the catalyst is selected from the group consisting of: $RuH_2(H_2)(N_2)(PR_3)_2$, $RuH_2(H_2)(R^2CN)(PR_3)_2$, $RuH_2(H_2)_2(PR_3)_2$, $RuH_2(N_2)_2(PR_3)_2$, $RuH_2(N_2)(R^2CN)(PR_3)_2$ and $RuH_2(R_2CN)_2(PR_3)_2$.

11. The process of claim 10 wherein the catalyst is selected from the group consisting: $RuH_2(H_2)_2(PCy_3)_2$, $RuH_2(N_2)_2(pCy_3)_2$, $RuH_2(H_2)_2(P\text{-}iPr_3)_2$ and $RuH_2(N_2)_2(P\text{-}iPr_3)_2$.

12. A process for the selective hydrogenation of a dinitrile, comprising the steps of:
   (a) contacting said dinitrile with gaseous hydrogen in the presence of a ruthenium complex catalyst having the formula $RuH_2L^3_2(PR_3)_2$, wherein:
   $PR_3$ is a phosphine ligand, wherein
   each R is a substituent independently selected from the group consisting of: H, a hydrocarbyl group, and an assembly of at least two hydrocarbyl groups connected by ether or an amine linkages; and
   each $L^3$ is a ligand independently selected from the group consisting of: $H_2$, $N_2$, $R^2CN$, and an additional equivalent of the $PR_3$ phosphine ligand, provided both $L^3$ are not $PR_3$;
   $R^2$ is a hydrocarbyl group;
   wherein each phosphine ligand is present as a separate ligand or cojoined with at least one other phosphine ligand; and
   (b) subsequently agitating the dinitrile, hydrogen and catalyst for an amount of time selected to favor yield of an aminonitrile over yield of a diamine.

13. The process of claim 12 wherein contact is made at a temperature of about 0° C. to about 200° C. at a pressure of about 100 kPa to about 15000 kPa, optionally in the presence of a solvent.

14. The process of claim 13 wherein the diamine is water-soluble and wherein the solvent is immiscible with water, further comprising separating the diamine by extraction with water from the solvent and the catalyst.

15. The process of claim 12 wherein the dinitrile is selected from the group consisting of: adiponitrile, 2-methylglutaronitrile and dodecanedinitrile.

16. The process of claim 12 wherein the catalyst is selected from the group consisting of: $RuH_2(H_2)(N_2)(PR_3)_2$, $RuH_2(H_2)(R^2CN)(PR_3)_2$, $RuH_2(H_2)_2(PR_3)_2$, $RuH_2(N_2)_2(PR_3)_2$, $RuH_2(N_2)(R^2CN)(PR_3)_2$ and $RuH_2(R^2CN)_2(PR_3)_2$.

17. The process of claim 16 wherein the catalyst is selected from the group consisting: $RuH_2(H_2)_2(PCy_3)_2$, $RuH_2(N_2)_2(pCy_3)_2$, $RuH_2(H_2)_2(P\text{-}iPr_3)_2$ and $RuH_2(N_2)_2(P\text{-}iPr_3)_2$.

18. A process for the reductive hydrolysis of an organic nitrile, comprising the steps of:
   (a) contacting said nitrile with gaseous hydrogen and water in the presence of a ruthenium complex catalyst having the formula $RuH_2L^3_2(PR_3)_2$, wherein:
   $PR_3$ is a phosphine ligand, wherein
   each R is a substituent independently selected from the group consisting of: H, a hydrocarbyl group, and an assembly of at least two hydrocarbyl groups connected by ether or an amine linkages; and
   each $L^3$ is a ligand independently selected from the group consisting of: $H_2$, $N_2$, $R^2CN$, and an additional equivalent of the $PR_3$ phosphine ligand, provided both $L^3$ are not $PR_3$;
   $R^2$ is a hydrocarbyl group;
   wherein each phosphine ligand is present as a separate ligand or cojoined with at least one other phosphine ligand; and (b) subsequently agitating the nitrile, water, hydrogen and catalyst to form an alcohol.

19. The process of claim 18 wherein contact is made at a temperature of about 0° C. to about 200° C. at a pressure of about 100 kPa to about 15000 kPa, optionally in the presence of a water-immiscible or homogenizing solvent.

20. The process of claim 19 wherein the alcohol is water-soluble and wherein the solvent is immiscible with water, further comprising separating the alcohol by extraction with water from the solvent and the catalyst.

21. The process of claim 18 wherein step (a) comprises at least 1 mole of water per mole of nitrile.

22. The process of claim 18 wherein step (a) comprises at least 30 to about 300 moles of water per mole of dinitrile.

23. The process of claim 18 wherein the nitrile is selected from the group consisting of: adiponitrile, 2-methylglutaronitrile, 3-cyano-methyliso-butyrate and dodecanedinitrile.

24. The process of claim 18 wherein the nitrite is a dinitrile and the alcohol is a diol.

25. The process of claim 18 wherein the catalyst is selected from the group consisting of: $RuH_2(H_2)(N_2)(PR_3)_2$, $RuH_2(H_2)(R^2CN)(PR_3)_2$, $RuH_2(H_2)_2(PR_3)_2$, $RuH_2(N_2)_2(PR_3)_2$, $RuH_2(N_2)(R^2CN)(PR_3)_2$ and $RuH_2(R^2CN)_2(PR_3)_2$.

26. The process of claim 25 wherein the catalyst is selected from the group consisting: $RuH_2(H_2)_2(PCy_3)_2$, $RuH_2(N_2)_2(PCy_3)_2$, $RuH_2(H_2)_2(P\text{-}ipr_3)2$ and $RuH_2(N_2)_2(P\text{-}iPr_3)_2$.

27. A process for the selective reductive hydrolysis of a dinitrile, comprising the steps of:
   (a) contacting said dinitrile with gaseous hydrogen and water in the presence of a ruthenium complex catalyst having the formula $RuH_2L^3{}_2(PR_3)_2$, wherein:
      $PR_3$ is a phosphine ligand, wherein
      each R is a substituent independently selected from the group consisting of: H, a hydrocarbyl group, and an assembly of at least two hydrocarbyl groups connected by ether or an amine linkages; and
      each $L^3$ is a ligand independently selected from the group consisting of: $H_2$, $N_2$, $R^2CN$, and an additional equivalent of the $PR_3$ phosphine ligand, provided both $L^3$ are not $PR_3$;
      $R^2$ is a hydrocarbyl group;
      wherein each phosphine ligand is present as a separate ligand or cojoined with at least one, other phosphine ligand; and
   (b) subsequently agitating the dinitrile, hydrogen, water and catalyst for an amount of time selected to favor yield of a hydroxynitrile over yield of a diol.

28. The process of claim 27 wherein contact is made at a temperature of about 0° C. to about 200° C. at a pressure of about 100 kPa to about 15000 kPa, optionally in the presence of a water-immiscible or homogenizing solvent.

29. The process of claim 28 wherein the hydroxynitrile is water-soluble and wherein the solvent is immiscible with water, further comprising separating the hydroxynitrile by extraction with water from the solvent and the catalyst.

30. The process of claim 27 wherein step (a) comprises at least 1 mole of water per mole of dinitrile.

31. The process of claim 27 wherein step (a) comprises at least 30 to about 300 moles of water per mole of dinitrile.

32. The process of claim 27 wherein the dinitrile is selected from the group consisting of: adiponitrile and dodecanedinitrile.

33. The process of claim 27 wherein the catalyst is selected from the group consisting of: $RuH_2(H_2)(N_2)(PR_3)_2$, $RuH_2(H_2)(R^2CN)(PR_3)_2$, $RuH_2(H_2)_2(PR_3)_2$, $RuH_2(N_2)_2(PR_3)_2$, $RuH_2(N_2)(R^2CN)(PR_{RuH2}(R^2CN)_2(PR_3)_2$.

34. The process of claim 33 wherein the catalyst is selected from the group consisting: $RuH_2(H_2)_2(PCy_3)_2$, $RuH_2(N_2)_2(PCy_3)_2$, $RuH_2(H_2)_2(P\text{-}iPr_3)_2$ and $RuH_2(N_2)_2(P\text{-}iPr_3)_2$.

35. A process for the hydrogenation of a nitro compound to a primary amine comprising the steps of:
   (a) contacting the nitro compound having at least one $NO_2$ group with gaseous hydrogen in the presence of a ruthenium complex catalyst having the formula $RuH_2L^3{}_2(PR_3)_2$, wherein:
      $PR_3$ is a phosphine ligand, wherein
      each R is a substituent independently selected from the group consisting of: H, a hydrocarbyl group, and an assembly of at least two hydrocarbyl groups connected by ether or an amine linkages; and
      each $L^3$ is a ligand independently selected from the group consisting of: $H_2$, $N_2$, $R^2CN$, and an additional equivalent of the $PR_3$ phosphine ligand, provided both $L^3$ are not $PR_3$;
      $R^2$ is a hydrocarbyl group;
      wherein each phosphine ligand is present as a separate ligand or cojoined with at least one other phosphine ligand; and
   (b) subsequently agitating the nitro compound, hydrogen and catalyst to form said primary amine.

36. The process of claim 35 wherein contact is made at a temperature of about 0° C. to about 200° C. at a pressure of about 100 kPa to about 15000 kPa, optionally in the presence of a solvent.

37. The process of claim 36 wherein the primary amine is water-soluble and wherein the solvent is immiscible with water, further comprising separating the primary amine by extraction with water from the solvent and the catalyst.

38. The process of claim 35 wherein the nitro compound is selected from the group consisting of: nitrobenzene, and 4,4'-dinitrodiphenyl-ether.

39. The process of claim 35 wherein the solvent is selected from the group consisting of: ammonia, tetrahydrofuran, t-butylmethyl-ether, toluene, n-butylamine, 2-methyl-pentamethylene diamine, hexzmethylene diamine, and n-amylamine.

40. The process of claim 35 wherein the catalyst is selected from the group consisting of: $RuH_2(H_2)(N_2)(PR_3)_2$, $RuH_2(H_2)(R^2CN)(PR_3)_2$, $RuH_2(H_2)_2(PR_3)2$, $RuH_2(N_2)_2(PR_3)_2$, $RuH_2(N_2)(R^2CN)(PR_3)_2$ and $RuH_2(R^2(C)_2(PR_3)_2$.

41. The process of claim 40 wherein the catalyst is selected from the group consisting: $RuH_2(H_2)_2(PCy_3)_2$, $RuH_2(N_2)_2(PCy_3)_2$, $RuH_2(H_2)_2(P\text{-}iPr_3)_2$ and $RuH_2(N_2)_2(P\text{-}iPr_3)_2$.

* * * * *